(12) United States Patent
Hebbel et al.

(10) Patent No.: US 6,852,537 B2
(45) Date of Patent: Feb. 8, 2005

(54) TRANSGENIC CIRCULATING ENDOTHELIAL CELLS

(75) Inventors: Robert P. Hebbel, North Oaks, MN (US); Yi Lin, St. Paul, MN (US); John S. Lollar, Decatur, GA (US)

(73) Assignee: Regents of the University of Minnesota Emory University, Atlanta, GA (US)

( * ) Notice: Subject to any disclaimer, the term of this patent is extended or adjusted under 35 U.S.C. 154(b) by 189 days.

(21) Appl. No.: 09/865,022

(22) Filed: May 24, 2001

(65) Prior Publication Data

US 2002/0042130 A1 Apr. 11, 2002

Related U.S. Application Data

(63) Continuation of application No. PCT/US99/28033, filed on Nov. 24, 1999.
(60) Provisional application No. 60/109,687, filed on Nov. 24, 1998.

(51) Int. Cl.$^7$ .............................. C12N 5/00; C12N 5/02; C12N 5/06; C12N 5/08
(52) U.S. Cl. ...................... 435/402; 435/395; 435/325; 435/355; 435/372; 435/404
(58) Field of Search .................................. 435/325, 363, 435/366, 372, 374, 377, 395, 404, 405, 406, 407, 355, 402

(56) References Cited

U.S. PATENT DOCUMENTS

| | | | |
|---|---|---|---|
| 5,132,223 A | 7/1992 | Levine et al. | 435/240.2 |
| 5,563,045 A | 10/1996 | Pittman et al. | 435/69.6 |
| 5,674,722 A | 10/1997 | Mulligan et al. | 435/172.3 |
| 5,980,887 A | 11/1999 | Isner et al. | 424/93.7 |
| 5,994,127 A | 11/1999 | Selden et al. | 435/325 |
| 6,140,123 A | * 10/2000 | Demetriou et al. | 435/374 |
| 6,352,555 B1 | * 3/2002 | Dzau et al. | 623/1.39 |

FOREIGN PATENT DOCUMENTS

| | | | |
|---|---|---|---|
| WO | 90/06997 | 12/1988 | C12N/15/00 |
| WO | 95/24427 | 3/1994 | C07K/14/755 |
| WO | 96/15777 | 11/1994 | A61K/31/00 |
| WO | 98/19712 | 11/1996 | A61K/48/00 |

OTHER PUBLICATIONS

Asahara et al., Isolation of putative progenitor endothelial cells for angiogenesis, 1997, SCIENCE, vol. 275, pp. 964–967.*
Gupta et al., A novel technique for culture of human dermal microvascular endothelial cells under either serum–free or serum–supplemented conditions: Isolation by panning and stimulation with vascular endothelial growth factor, 1997, Experimental Cell Research, vol. 230, pp. 244–251.*
Solovey et al., Circulating activated endothelial cells in sickle cell anemia, 1997, The New England Journal of Medicine, vol. 337, pp. 1584–1590.*
Gnatenko, D., et al., "An adeno–associated/adenovirus hybrid vector generates high–level human factor VIII in vitro", *40th Annual Meeting of the American Society of Hematology*, 92 (10), Suppl. 1, Part 1–2, Abstract No. 586, Miami Beach, FL, p. 146A, (Dec. 1998).
Lin, Y., et al., "Circulating endothelial cells are from vessel wall, but peripheral blood endothelial outgrowth is from a marrow–derived cell", *40th Annual Meeting of the American Society of Hematology*, 92 (10) Suppl 1, Part 1–2, Abstract No. 614, Miami Beach, FL, p. 152A, (Dec. 1998).
Senger, D.R., et al., "Angiogenesis promoted by vascular endothelial growth factor: regulation through alphalbeta1 and alpha2beta1 integrins", *PNAS, USA*, 94, (25), pp. 13612–13617, (Dec. 9, 1997).
Shi, Q., et al., "Evidence for circulating bone marrow–derived endothelial cells", *Blood*, 92 (2), pp. 362–367, (Jul. 1998).
Solovey, A., et al., "Tissue factor expression by endothelial cells in sickle cell anemia", *J. of Clin. Investigation*, 101 (9), pp. 1899–1904, (May 1, 1998).

* cited by examiner

*Primary Examiner*—David Guzo
*Assistant Examiner*—Quang Nguyen
(74) *Attorney, Agent, or Firm*—Schwegman, Lundberg, Woessner & Kluth, P.A.

(57) ABSTRACT

A process is provided for expanding the population of endothelial cells obtained from peripheral blood which can be transformed with a vector comprising a DNA sequence encoding a preselected bioactive polypeptide. The resulting transgenic endothelial cells are useful to biocompatibilize implantable medical devices or can be used directly, as for gene therapy.

17 Claims, 13 Drawing Sheets hFVIII/SQ/egfp, HF8SQgfp.gp, original HB- with B-domain SQ insert based on Lind et al, Eur J Biochem, 232, p21 primer sequence, containing eGFP protein sequence $ ATGCAAATAGAGCTCTCCACCTGCTTCTTTCTGTGCCTTTTGCGAT
TCTGCTTT
AGTGCCACCAGAAGATACTACCTGGGTGCAGTGGAACTGTCATGG
GACTATATGCAAAGTGA
TCTCGGTGAGCTGCCTGTGGACGCAAGATTTCCTCCTAGAGTGCC
AAAATCTTTTCCATTCAA
CACCTCAGTCGTGTACAAAAAGACTCTGTTTGTAGAATTCACGGTT
CACCTTTTCAACATCGC
TAAGCCAAGGCCACCCTGGATGGGTCTGCTAGGTCCTACCATCCA
GGCTGAGGTTTATGATAC
AGTGGTCATTACACTTAAGAACATGGCTTCCCATCCTGTCAGTCTT
CATGCTGTTGGTGTATCC
TACTGGAAAGCTTCTGAGGGAGCTGAATATGATGATCAGACCAGT
CAAAGGGAGAAAGAAGA
TGATAAAGTCTTCCCTGGTGGAAGCCATACATATGTCTGGCAGGTC
CTGAAAGAGAATGGTCC
AATGGCCTCTGACCCACTGTGCCTTACCTACTCATATCTTTCTCAT
GTGGACCTGGTAAAAGA
CTTGAATTCAGGCCTCATTGGAGCCCTACTAGTATGTAGAGAAGG
GAGTCTGGCCAAGGAAA
AGACACAGACCTTGCACAAATTTATACTACTTTTTGCTGTATTTGA
TGAAGGGAAAAGTTGGC
ACTCAGAAACAAAGAACTCCTTGATGCAGGATAGGGATGCTGCAT
CTGCTCGGGCCTGGCCT
AAAATGCACACAGTCAATGGTTATGTAAACAGGTCTCTGCCAGGT
CTGATTGGATGCCACAG
GAAATCAGTCTATTGGCATGTGATTGGAATGGGCACCACTCCTGA
AGTGCACTCAATATTCCT
CGAAGGTCACACATTTCTTGTGAGGAACCATCGCCAGGCGTCCTT
GGAAATCTCGCCAATAAC
TTTCCTTACTGCTCAAACACTCTTGATGGACCTTGGACAGTTTCTA
CTGTTTTGTCATATCTCT
TCCCACCAACATGATGGCATGGAAGCTTATGTCAAAGTAGACAGC
TGTCCAGAGGAACCCCA
ACTACGAATGAAAAATAATGAAGAAGCGGAAGACTATGATGATGA
TCTTACTGATTCTGAAA
TGGATGTGGTCAGGTTTGATGATGACAACTCTCCTTCCTTTATCCA
AATTCGCTCAGTTGCCA
AGAAGCATCCTAAAACTTGGGTACATTACATTGCTGCTGAAGAGG
AGGACTGGGACTATGCT
CCCTTAGTCCTCGCCCCCGATGACAGAAGTTATAAAAGTCAATATT
TGAACAATGGCCCTCAG
CGGATTGGTAGGAAGTACAAAAAAAGTCCGATTTATGGCATACACA
GATGAAACCTTTAAGAC
TCGTGAAGCTATTCAGCATGAATCAGGAATCTTGGGACCTTTACTT
TATGGGGAAGTTGGAGA
CACACTGTTGATTATATTTAAGAATCAAGCAAGCAGACCATATAA
CATCTACCCTCACGGAAT
CACTGATGTCCGTCCTTTGTATTCAAGGAGATTACCAAAAGGTGTA
AAACATTTGAAGGATTT
TCCAATTCTGCCAGGAGAAATATTCAAATATAAATGGACAGTGAC

FIG. 3A

```
TGTAGAAGATGGGCCAA
CTAAATCAGATCCTCGGTGCCTGACCCGCTATTACTCTAGTTTCGT
TAATATGGAGAGAGATC
TAGCTTCAGGACTCATTGGCCCTCTCCTCATCTGCTACAAAGAATC
TGTAGATCAAAGAGGAA
ACCAGATAATGTCAGACAAGAGGAATGTCATCCTGTTTTCTGTATT
TGATGAGAACCGAAGCT
GGTACCTCACAGAGAATATACAACGCTTTCTCCCCAATCCAGCTG
GAGTGCAGCTTGAGGATC
CAGAGTTCCAAGCCTCCAACATCATGCACAGCATCAATGGCTATG
TTTTTGATAGTTTGCAGT
TGTCAGTTTGTTTGCATGAGGTGGCATACTGGTACATTCTAAGCAT
TGGAGCACAGACTGACT
TCCTTTCTGTCTTCTTCTCTGGATATACCTTCAAACACAAAATGGTC
TATGAAGACACACTCAC
CCTATTCCCATTCTCAGGAGAAACTGTCTTCATGTCGATGGAAAAC
CCAGGTCTATGGATTCT
GGGGTGCCACAACTCAGACTTTCGGAACAGAGGCATGACCGCCTT
ACTGAAGGTTTCTAGTTG
TGACAAGAACACTGGTGATTATTACGAGGACAGTTATGAAGATAT
TTCAGCATACTTGCTGAG
TAAAAACAATGCCATTGAACCTAGG
AGCTTCTCTCAGAATATGGTGAGCAAGGGCGAGGAGC
TGTTCACCGG GGTGGTGCCC
ATCCTGGTCG AGCTGGACGG CGACGTAAAC GGCCACAAGT
TCAGCGTGTC CGGCGAGGGC
GAGGGCGATG CCACCTACGG CAAGCTGACC CTGAAGTTCA
TCTGCACCAC CGGCAAGCTG
CCCGTGCCCT GGCCCACCCT CGTGACCACC CTGACCTACG
GCGTGCAGTG CTTCAGCCGC
TACCCCGACC ACATGAAGCA GCACGACTTC TTCAAGTCCG
CCATGCCCGA AGGCTACGTC
CAGGAGCGCA CCATCTTCTT CAAGGACGAC GGCAACTACA
AGACCCGCGC CGAGGTGAAG
TTCGAGGGCG ACACCCTGGT GAACCGCATC GAGCTGAAGG
GCATCGACTT CAAGGAGGAC
GGCAACATCC TGGGGCACAA GCTGGAGTAC AACTACAACA
GCCACAACGT CTATATCATG
GCCGACAAGC AGAAGAACGG CATCAAGGTG AACTTCAAGA
TCCGCCACAA CATCGAGGAC
GGCAGCGTGC AGCTCGCCGA CCACTACCAG CAGAACACCC
CCATCGGCGA CGGCCCCGTG
CTGCTGCCCG ACAACCACTA CCTGAGCACC CAGTCCGCCC
TGAGCAAAGA CCCCAACGAG
AAGCGCGATC ACATGGTCCT GCTGGAGTTC GTGACCGCCG
CCGGGATCAC TCTCGGCATG
GACGAGCTGT ACAAGTATCCACCAGTCTTGAAACGCCATCAACGG
GAAATAACTCGTACTACTCT
TCAGTCAGATCAAGAGG
AAATTGACTATGATGATACCATATCAGTTGAAATGAAGAAGGAAG
ATTTTGACATTTATGATG
AGGATGAAAATCAGAGCCCCCGCAGCTTTCAAAAGAAAACACGAC
ACTATTTTATTGCTGCA
GTGGAGAGGCTCTGGGATTATGGGATGAGTAGCTCCCCACATGTT
```

FIG. 3B

```
CTAAGAAACAGGGCTCA
GAGTGGCAGTGTCCCTCAGTTCAAGAAAGTTGTTTTCCAGGAATTT
ACTGATGGCTCCTTTAC
TCAGCCCTTATACCGTGGAGAACTAAATGAACATTTGGGACTCCT
GGGGCCATATATAAGAG
CAGAAGTTGAAGATAATATCATGGTAACTTTCAGAAATCAGGCCT
CTCGTCCCTATTCCTTCT
ATTCTAGCCTTATTTCTTATGAGGAAGATCAGAGGCAAGGAGCAG
AACCTAGAAAAAACTTT
GTCAAGCCTAATGAAACCAAAACTTACTTTTGGAAAGTGCAACAT
CATATGGCACCCACTAA
AGATGAGTTTGACTGCAAAGCCTGGGCTTATTTCTCTGATGTTGAC
CTGGAAAAAGATGTGCA
CTCAGGCCTGATTGGACCCCTTCTGGTCTGCCACACTAACACACTG
AACCCTGCTCATGGGAG
ACAAGTGACAGTACAGGAATTTGCTCTGTTTTTCACCATCTTTGAT
GAGACCAAAAGCTGGTA
CTTCACTGAAAATATGGAAAGAAACTGCAGGGCTCCCTGCAATAT
CCAGATGGAAGATCCCA
CTTTTAAAGAGAATTATCGCTTCCATGCAATCAATGGCTACATAAT
GGATACACTACCTGGCT
TAGTAATGGCTCAGGATCAAAGGATTCGATGGTATCTGCTCAGCA
TGGGCAGCAATGAAAAC
ATCCATTCTATTCATTTCAGTGGACATGTGTTCACTGTACGAAAAA
AAGAGGAGTATAAAATG
GCACTGTACAATCTCTATCCAGGTGTTTTTGAGACAGTGGAAATGT
TACCATCCAAAGCTGGA
ATTTGGCGGGTGGAATGCCTTATTGGCGAGCATCTACATGCTGGG
ATGAGCACACTTTTTCTG
GTGTACAGCAATAAGTGTCAGACTCCCCTGGGAATGGCTTCTGGA
CACATTAGAGATTTTCAG
ATTACAGCTTCAGGACAATATGGACAGTGGGCCCCAAAGCTGGCC
AGACTTCATTATTCCGG
ATCAATCAATGCCTGGAGCACCAAGGAGCCCTTTTCTTGGATCAA
GGTGGATCTGTTGGCACC
AATGATTATTCACGGCATCAAGACCCAGGGTGCCCGTCAGAAGTT
CTCCAGCCTCTACATCTC
TCAGTTTATCATCATGTATAGTCTTGATGGGAAGAAGTGGCAGACT
TATCGAGGAAATTCCAC
TGGAACCTTAATGGTCTTCTTTGGCAATGTGGATTCATCTGGGATA
AAACACAATATTTTTAA
CCCTCCAATTATTGCTCGATACATCCGTTTGCACCCAACTCATTAT
AGCATTCGCAGCACTCTT
CGCATGGAGTTGATGGGCTGTGATTTAAATAGTTGCAGCATGCCA
TTGGGAATGGAGAGTAA
AGCAATATCAGATGCACAGATTACTGCTTCATCCTACTTTACCAAT
ATGTTTGCCACCTGGTC
TCCTTCAAAAGCTCGACTTCACCTCCAAGGGAGGAGTAATGCCTG
GAGACCTCAGGTGAATA
ATCCAAAAGAGTGGCTGCAAGTGGACTTCCAGAAGACAATGAAAG
TCACAGGAGTAACTACT
CAGGGAGTAAAATCTCTGCTTACCAGCATGTATGTGAAGGAGTTC
CTCATCTCCAGCAGTCAA
GATGGCCATCAGTGGACTCTCTTTTTTCAGAATGGCAAAGTAAAG
```

FIG. 3C

GTTTTTCAGGGAAATCAA
GACTCCTTCACACCTGTGGTGAACTCTCTAGACCCACCGTTACTGA
CTCGCTACCTTCGAATT
CACCCCCAGAGTTGGGTGCACCAGATTGCCCTGAGGATGGAGGTT
CTGGGCTGCGAGGCACA
GGACCTCTACTGA*

FIG. 3D

GAATTCCGGAATTCCAGCTTGCTGTGGAATGTGTGTCAGTTAGGGTGTGGAAAGTCCCCAGG
CTCCCCAGCAGGCAGAAGTATGCAAAGCATGCATCTCAATTAGTCAGCAACCAGGTGTGGAAAG
TCCCCAGGCTCCCCAGCAGGCAGAAGTATGCAAAGCATGCATCTCAATTAGTCAGCAACCATAG
TCCCGCCCCTAACTCCGCCCATCCCGCCCCTAACTCCGCCCAGTTCCGCCCATTCTCCGCCCCA
TGGCTGACTAATTTTTTTTATTTATGCAGAGGCCGAGGCCGCCTCGGCCTCTGAGCTATTCCAG
AAGTAGTGAGGAGGCTTTTTTGGAGGGGTCCTCCTCGTATAGAAACTCGGACCACTCTGAGACG
AAGGCTCGCGTCCAGGCCAGCACGAAGGAGGCTAAGTGGGAGGGGTAGCGGTCGTTGTCCACTA
GGGGGTCCACTCGCTCCAGGGTGTGAAGACACATGTCGCCCTCTTCGGCATCAAGGAAGGTGAT
TGGTTTATAGGTGTAGGCCACGTGACCGGGTGTTCCTGAAGGGGGGTATAAAAGGGGGTGGGG
GCGCGTTCGTCCTCACTCTCTTCCGCATCGCTGTCTGCGAGGGCCAGCTGTTGGGCTCGCGGTT
GAGGACAAACTCTTCGCGGTCTTTCCAGTACTCTTGGATCGGAAACCCGTCGGCCTCCGAACGG
TACTCCGCCACCGAGGGACCTGAGCGAGTCCGCATCGACCGGATCGGAAAACCTCTCGAGCCAC
C
ATGCAAATAGAGCTCTCCACCTGCTTCTTTCTGTGCCTTTTGCGATTCTGCTTTAGTGCCACCA
GAAGATACTACCTGGGTGCAGTGGAACTGTCATGGGACTATATGCAAAGTGATCTCGGTGAGCT
GCCTGTGGACGCAAGATTTCCTCCTAGAGTGCCAAAATCTTTTCCATTCAACACCTCAGTCGTG
TACAAAAAGACTCTGTTTGTAGAATTCACGGTTCACCTTTTCAACATCGCTAAGCCAAGGCCAC
CCTGGATGGGTCTGCTAGGTCCTACCATCCAGGCTGAGGTTTATGATACAGTGGTCATTACACT
TAAGAACATGGCTTCCCATCCTGTCAGTCTTCATGCTGTTGGTGTATCCTACTGGAAAGCTTCT
GAGGGAGCTGAATATGATGATCAGACCAGTCAAAGGGAGAAAGAAGATGATAAAGTCTTCCCTG
GTGGAAGCCATACATATGTCTGGCAGGTCCTGAAAGAGAATGGTCCAATGGCCTCTGACCCACT
GTGCCTTACCTACTCATATCTTTCTCATGTGGACCTGGTAAAAGACTTGAATTCAGGCCTCATT
GGAGCCCTACTAGTATGTAGAGAAGGGAGTCTGGCCAAGGAAAAGACACAGACCTTGCACAAAT
TTATACTACTTTTTGCTGTATTTGATGAAGGGAAAAGTTGGCACTCAGAAACAAAGAACTCCTT
GATGCAGGATAGGGATGCTGCATCTGCTCGGGCCTGGCCTAAAATGCACACAGTCAATGGTTAT
GTAAACAGGTCTCTGCCAGGTCTGATTGGATGCCACAGGAAATCAGTCTATTGGCATGTGATTG
GAATGGGCACCACTCCTGAAGTGCACTCAATATTCCTCGAAGGTCACACATTTCTTGTGAGGAA
CCATCGCCAGGCGTCCTTGGAAATCTCGCCAATAACTTTCCTTACTGCTCAAACACTCTTGATG
GACCTTGGACAGTTTCTACTGTTTTGTCATATCTCTTCCCACCAACATGATGGCATGGAAGCTT
ATGTCAAAGTAGACAGCTGTCCAGAGGAACCCCAACTACGAATGAAAAATAATGAAGAAGCGGA
AGACTATGATGATGATCTTACTGATTCTGAAATGGATGTGGTCAGGTTTGATGATGACAACTCT
CCTTCCTTTATCCAAATTCGCTCAGTTGCCAAGAAGCATCCTAAAACTTGGGTACATTACATTG
CTGCTGAAGAGGAGGACTGGGACTATGCTCCCTTAGTCCTCGCCCCCGATGACAGAAGTTATAA
AAGTCAATATTTGAACAATGGCCCTCAGCGGATTGGTAGGAAGTACAAAAAAGTCCGATTTATG
GCATACACAGATGAAACCTTTAAGACTCGTGAAGCTATTCAGCATGAATCAGGAATCTTGGGAC
CTTTACTTTATGGGGAAGTTGGAGACACACTGTTGATTATATTTAAGAATCAAGCAAGCAGACC
ATATAACATCTACCCTCACGGAATCACTGATGTCCGTCCTTTGTATTCAAGGAGATTACCAAAA

FIG. 4A

```
GGTGTAAAACATTTGAAGGATTTTCCAATTCTGCCAGGAGAAATATTCAAATATAAATGGACAG
TGACTGTAGAAGATGGGCCAACTAAATCAGATCCTCGGTGCCTGACCCGCTATTACTCTAGTTT
CGTTAATATGGAGAGAGATCTAGCTTCAGGACTCATTGGCCCTCTCCTCATCTGCTACAAAGAA
TCTGTAGATCAAAGAGGAAACCAGATAATGTCAGACAAGAGGAATGTCATCCTGTTTTCTGTAT
TTGATGAGAACCGAAGCTGGTACCTCACAGAGAATATACAACGCTTTCTCCCCAATCCAGCTGG
AGTGCAGCTTGAGGATCCAGAGTTCCAAGCCTCCAACATCATGCACAGCATCAATGGCTATGTT
TTTGATAGTTTGCAGTTGTCAGTTTGTTTGCATGAGGTGGCATACTGGTACATTCTAAGCATTG
GAGCACAGACTGACTTCCTTTCTGTCTTCTTCTCTGGATATACCTTCAAACACAAAATGGTCTA
TGAAGACACACTCACCCTATTCCCATTCTCAGGAGAAACTGTCTTCATGTCGATGGAAAACCCA
GGTCTATGGATTCTGGGGTGCCACAACTCAGACTTTCGGAACAGAGGCATGACCGCCTTACTGA
AGGTTTCTAGTTGTGACAAGAACACTGGTGATTATTACGAGGACAGTTATGAAGATATTTCAGC
ATACTTGCTGAGTAAAAACAATGCCATTGAACCTAGGAGCTTCTCTCAGAATCCACCAGTCTTG
AAACGCCATCAACGGGAAATAACTCGTACTACTCTTCAGTCAGATCAAGAGGAAATTGACTATG
ATGATACCATATCAGTTGAAATGAAGAAGGAAGATTTTGACATTTATGATGAGGATGAAAATCA
GAGCCCCCGCAGCTTTCAAAAGAAAACACGACACTATTTTATTGCTGCAGTGGAGAGGCTCTGG
GATTATGGGATGAGTAGCTCCCCACATGTTCTAAGAAACAGGGCTCAGAGTGGCAGTGTCCCTC
AGTTCAAGAAAGTTGTTTTCCAGGAATTTACTGATGGCTCCTTTACTCAGCCCTTATACCGTGG
AGAACTAAATGAACATTTGGGACTCCTGGGGCCATATATAAGAGCAGAAGTTGAAGATAATATC
ATGGTAACTTTCAGAAATCAGGCCTCTCGTCCCTATTCCTTCTATTCTAGCCTTATTTCTTATG
AGGAAGATCAGAGGCAAGGAGCAGAACCTAGAAAAAACTTTGTCAAGCCTAATGAAACCAAAAC
TTACTTTTGGAAAGTGCAACATCATATGGCACCCACTAAAGATGAGTTTGACTGCAAAGCCTGG
GCTTATTTCTCTGATGTTGACCTGGAAAAAGATGTGCACTCAGGCCTGATTGGACCCCTTCTGG
TCTGCCACACTAACACACTGAACCCTGCTCATGGGAGACAAGTGACAGTACAGGAATTTGCTCT
GTTTTTCACCATCTTTGATGAGACCAAAAGCTGGTACTTCACTGAAAATATGGAAAGAAACTGC
AGGGCTCCCTGCAATATCCAGATGGAAGATCCCACTTTTAAAGAGAATTATCGCTTCCATGCAA
TCAATGGCTACATAATGGATACACTACCTGGCTTAGTAATGGCTCAGGATCAAAGGATTCGATG
GTATCTGCTCAGCATGGGCAGCAATGAAAACATCCATTCTATTCATTTCAGTGGACATGTGTTC
ACTGTACGAAAAAAAGAGGAGTATAAAATGGCACTGTACAATCTCTATCCAGGTGTTTTTGAGA
CAGTGGAAATGTTACCATCCAAAGCTGGAATTTGGCGGGTGGAATGCCTTATTGGCGAGCATCT
ACATGCTGGGATGAGCACACTTTTTCTGGTGTACAGCAATAAGTGTCAGACTCCCCTGGGAATG
GCTTCTGGACACATTAGAGATTTTCAGATTACAGCTTCAGGACAATATGGACAGTGGGCCCCAA
AGCTGGCCAGACTTCATTATTCCGGATCAATCAATGCCTGGAGCACCAAGGAGCCCTTTTCTTG
GATCAAGGTGGATCTGTTGGCACCAATGATTATTCACGGCATCAAGACCCAGGGTGCCCGTCAG
AAGTTCTCCAGCCTCTACATCTCTCAGTTTATCATCATGTATAGTCTTGATGGGAAGAAGTGGC
AGACTTATCGAGGAAATTCCACTGGAACCTTAATGGTCTTCTTTGGCAATGTGGATTCATCTGG
GATAAAACACAATATTTTTAACCCTCCAATTATTGCTCGATACATCCGTTTGCACCCAACTCAT
TATAGCATTCGCAGCACTCTTCGCATGGAGTTGATGGGCTGTGATTTAAATAGTTGCAGCATGC
CATTGGGAATGGAGAGTAAAGCAATATCAGATGCACAGATTACTGCTTCATCCTACTTTACCAA
TATGTTTGCCACCTGGTCTCCTTCAAAAGCTCGACTTCACCTCCAAGGGAGGAGTAATGCCTGG
AGACCTCAGGTGAATAATCCAAAAGAGTGGCTGCAAGTGGACTTCCAGAAGACAATGAAAGTCA
CAGGAGTAACTACTCAGGGAGTAAAATCTCTGCTTACCAGCATGTATGTGAAGGAGTTCCTCAT
CTCCAGCAGTCAAGATGGCCATCAGTGGACTCTCTTTTTTCAGAATGGCAAAGTAAAGGTTTTT
CAGGGAAATCAAGACTCCTTCACACCTGTGGTGAACTCTCTAGACCCACCGTTACTGACTCGCT
ACCTTCGAATTCACCCCCAGAGTTGGGTGCACCAGATTGCCCTGAGGATGGAGGTTCTGGGCTGC
GAGGCACAGGACCTCTACTGA
GGGCGGCCGCTGCAGCACCTGCCACTGCCGTCACCTCTCCCTCCTCAGCTCCAGGGCAGTGTCC
CTCCCTGGCTTGCCTTCTACCTTTGTGCTAAATCCTAGCAGACACTGCCTTGAAGCCTCCTGAA
TTAACTATCATCAGTCCTGCATTTCTTTGGTGGGGGCCAGGAGGGTGCATCCAATTTAACTTA
ACTCTTACCTATTTTCTGCAGCTGCTCCCAGATTACTCCTTCCTTCCAATATAACTAGGCAAAA
AGAAGTGAGGAGAAACCTGCATGAAAGCATTCTTCCCTGAAAAGTTAGGCCTCTCAGAGTCACC
ACTTCCTCTGTTGTAGAAAAACTATGTGATGAAACTTTGAAAAAGATATTTATGATGTTAACAT
TTCAGGTTAAGCCTCATACGTTTAAAATAAAACTCTCAGTTGTTTATTATCCTGATCAAGCATG
GAACAAAGCATGTTTCAGGATCAGATCAATACAATCTTGGAGTCAAAAGGCAAATCATTTGGAC
AATCTGCAAAATGGAGAGAATACAATAACTACTACAGTAAAGTCTGTTTCTGCTTCCTTACACA
TAGATATAATTATGTTATTTAGTCATTATGAGGGGCACATTCTTATCTCCAAAACTAGCATTCT
TAAACTGAGAATTATAGATGGGGTTCAAGAATCCCTAAGTCCCCTGAAATTATATAAGGCATTC
TGTATAAATGCAAATGTGCATTTTTCTGACGAGTGTCCATAGATATGGGACATATGACGTGAGC
```

FIG. 4B

```
TCAGATCTTTGTGAAGGAACCTTACTTCTGTGGTGTGACATAATTGGACAAACTACCTACAGAG
ATTTAAAGCTCTAAGGTAAATATAAAATTTTTAAGTGTATAATGTGTTAAACTACTGATTCTAA
TTGTTTGTGTATTTTAGATTCCAACCTATGGAACTGATGAATGGGAGCAGTGGTGGAATGCCTT
TAATGAGGAAAACCTGTTTTGCTCAGAAGAAATGCCATCTAGTGATGATGAGGCTACTGCTGAG
TGTGAACATTCTACTCCTCCAAAAAAGAAGAGAAAGGTAGAAGACCCCAAGGACTTTCCTTCAG
AATTGCTAAGTTTTTTGAGTCATGCTGTGTTTAGTAATAGAACTCTTGCTTGCTTTGCTATTTA
CACCACAAAGGAAAAAGCTGCACTGCTATACAAGAAAATTATGGAAAAATATTCTGTAACCTTT
ATAAGTAGGCATAACAGTTATAATCATAACATACTGTTTTTTCTTACTCCACACAGGCATAGAG
TGTCTGCTATTAATAACTATGCTCAAAAATTGTGTACCTTTAGCTTTTTAATTTGTAAAGGGGT
TAATAAGGAATATTTGATGTATAGTGCCTTGACTAGAGATCATAATCAGCCATACCACATTTGT
AGAGGTTTTACTTGCTTTAAAAAACCTCCCACACCTCCCCCTGAACCTGAAACATAAAATGAAT
GCAATTGTTGTTGTTAACTTGTTTATTGCAGCTTATAATGGTTACAAATAAAGCAATAGCATCA
CAAATTTCACAAATAAAGCATTTTTTTCACTGCATTCTAGTTGTGGTTTGTCCAAACTCATCAA
TGTATCTTATCATGTCTGGATCCTCTACGCCGGACGCATCGTGGCCGGCATCACCGGCGCCACA
GGTGCGGTTGCTGGCGCCTATATCGCCGACATCACCGATGGGAAGATCGGCTCGCCACTTCG
GGCTCATGAGCGCTTGTTTCGGCGTGGGTATGGTGGCAGGCCCGTGGCCGGGGACTGTTGGGC
GCCATCTCCTTGCATGCACCATTCCTTGCGGCGGCGGTGCTCAACGGCCTCAACCTACTACTGG
GCTGCTTCCTAATGCAGGAGTCGCATAAGGGAGAGCGTCGAAATTCTCATGTTTGACAGCTTAT
CATCGGCGCAGCACCATGGCCTGAAATAACCTCTGAAAGAGGAACTTGGTTAGGTACCTTCTGA
GGCGGAAAGAACCAGCTGTGGAATGTGTGTCAGTTAGGGTGTGGAAAGTCCCCAGGCTGGGGAG
CAGGCAGAAGTATGCAAAGCATGCATCTCAATTAGTCAGCAACCAGGTGTGGAAAGTCCCCAGG
CTCCCCAGCAGGCAGAAGTATGCAAAGCATGCATCTCAATTAGTCAGCAACCATAGTCCCGCCC
CTAACTCCGCCCATCCCGCCCCTAACTCCGCCCAGTTCCGCCCATTCTCCGCCCCATGGCTGAC
TAATTTTTTTTATTTATGCAGAGGCCGAGGCCGCCTCGGCCTCTGAGCTATTCCAGCCGTAGTG
AGGAGGCTTTTTTGGAGGCCTAGGCTTTTGCAAAAAGCTTCACGCTGCCGCAAGCACTCAGGGC
GCAAGGGCTGCTAAAGGAAGCGGAACACGTAGAAAGCCAGTCCGCAGAAACGGTGCTGACCCCG
GATGAATGTCAGCTACTGGGCTATCTGGACAAGGGAAAACGCAAGCGCAAAGAGAAAGCAGGTA
GCTTGCAGTGGGCTTACATGGCGATAGCTAGACTGGGCGGTTTTATGGACAGCAAGCGAACCGG
AATTGCCAGCTGGGGCGCCCTCTGGTAAGGTTGGGAAGCCCTGCAAAGTAAACTGGATGGCTTT
CTTGCCGCCAAGGATCTGATGGCGCAGGGGATCAAGATCTGATCAAGAGACAGGATGAGGATCG
TTTCGCATGATTGAACAAGATGGATTGCACGCAGGTTCTCCGGCCGCTTGGGTGGAGAGGCTAT
TCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGAC
GAGGCAGCGCGGCTATCGTGGCTGGCCACGACGGGCGTTCCTTGCGCAGCTGTGCTCGACGTTG
TCACTGAAGCGGGAAGGGACTGGCTGCTATTGGGCGAAGTGCCGGGGCAGGATCTCCTGTCATC
TCACCTTGCTCCTGCCGAGAAAGTATCCATCATGGCTGATGCAATGCGGCGGCTGCATACGCTT
GATCCGGCTACCTGCCCATTCGACCACCAAGCGAAACATCGCATCGAGCGAGCACGTACTCGGA
TGGAAGCCGGTCTTGTCGATCAGGATGATCTGGACGAAGAGCATCAGGGGCTCGCGCCAGCCGA
ACTGTTCGCCAGGCTCAAGGCGCGCATGCCCGACGGCGAGGATCTCGTCGTGACCCATGGCGAT
GCCTGCTTGCCGAATATCATGGTGGAAAATGGCCGCTTTTCTGGATTCATCGACTGTGGCCGGC
TGGGTGTGGCGGACCGCTATCAGGACATAGCGTTGGCTACCCGTGATATTGCTGAAGAGCTTGG
CGGCGAATGGGCTGACCGCTTCCTCGTGCTTTACGGTATCGCCGCTCCCGATTCGCAGCGCATC
GCCTTCTATCGCCTTCTTGACGAGTTCTTCTGAGCGGGACTCTGGGGTTCGAAATGACCGACCA
AGCGACGCCCAACCTGCCATCACGAGATTTCGATTCCACCGCCGCCTTCTATGAAAGGTTGGGC
TTCGGAATCGTTTTCCGGGACGCCGGCTGGATGATCCTCCAGCGCGGGATCTCATGCTGGAGT
TCTTCGCCCACCCCGGGCTCGATCCCCTCGCGAGTTGGTTCAGCTGCTGCCTGAGGCTGGACGA
CCTCGCGGAGTTCTACCGGCAGTGCAAATCCGTCGGCATCCAGGAAACCAGCAGCGGCTATCCG
CGCATCCATGCCCCCGAACTGCAGGAGTGGGGAGGCACGATGGCCGCTTTGGTCCCGGATCTTT
GTGAAGGAACCTTACTTCTGTGGTGTGACATAATTGGAGAAACTACCTACAGAGATTTAAAGCT
CTAAGGTAAATATAAAATTTTTAAGTGTATAATGTGTTAAACTACTGATTCTAATTGTTTGTGT
ATTTTAGATTCCAACCTATGGAACTGATGAATGGGAGCAGTGGTGGAATGCCTTTAATGAGGAA
AACCTGTTTTGCTCAGAAGAAATGCCATCTAGTGATGATGAGGCTACTGCTGACTCTCAACATT
CTACTCCTCCAAAAAAGAAGAGAAAGGTAGAAGACCCCAAGGACTTTCCTTCAGAATTGCTAAG
TTTTTTGAGTCATGCTGTGTTTAGTAATAGAACTCTTGCTTGCTTTGCTATTTACACCACAAAG
GAAAAAGCTGCACTGCTATACAAGAAAATTATGGAAAAATATTCTGTAACCTTTATAAGTAGGC
ATAACAGTTATAATCATAACATACTGTTTTTTCTTACTCCACACAGGCATAGAGTGTCTGCTAT
TAATAACTATGCTCAAAAATTGTGTACCTTTAGCTTTTTAATTTGTAAAGGGGTTAATAAGGAA
```

FIG. 4C

```
TATTTGATGTATAGTGCCTTGACTAGAGATCATAATCAGCCATACCACATTTGTAGAGGTTTTA
CTTGCTTTAAAAAACCTCCCACACCTCCCCCTGAACCTGAAACATAAAATGAATGCAATTGTTG
TTGTTAACTTGTTTATTGCAGCTTATAATGGTTACAAATAAAGCAATAGCATCACAAATTTCAC
AAATAAAGCATTTTTTTCACTGCATTCTAGTTGTGGTTTGTCCAAACTCATCAATGGTATCTTA
TCATGTCTGGATCTCGACCGAGCCCTTGAGAGCCTTCAACCCAGTCAGCTCCTTCCGGTGGGCG
CGGGGCATGACTATCGTCGCCGCACTTATGACTGTCTTCTTTATCATGCAACTCGTAGGACAGG
TGCCGGCAGCGCTCTGGGTCATTTTCGGCGAGGACCGCTTTCGCTGGAGCGCGACGATGATCGG
CCTGTCGCTTGCGGTATTCGGAATCTTGCACGCCCTCGCTCAAGCCTTCGTCACTGGTCCCGCC
ACCAAACGTTTCGGCGAGAAGCAGGCCATTATCGCCGGCATGGCGGCCGACGCGCTGGGCTACG
TCTTGCTGGCGTTCGCGACGCGAGGCTGGATGGCCTTCCCCATTATGATTCTTCTCGCTTCCGG
CGGCATCGGGATGCCCGCGTTGCAGGCCATGCTGTCCAGGCAGGTAGATGACGACCATCAGGGA
CAGCTTCAAGGATCGCTCGCGGCTCTTACCAGCCTAACTTCGATCACTGGACCGCTGATCGTCA
CGGCGATTTATGCCGCCTCGGCGAGCACATGGAACGGGTTGGCATGGATTGTAGGCGCCGCCCT
ATACCTTGTCTGCCTCCCCGCGTTGCGTCGCGGTGCATGGAGCCGGGCCACCTCGACCTGAATG
GAAGCCGGCGGCACCTCGCTAACGGATTCACCACTCCAAGAATTGGAGCCAATCAATTCTTGCG
GAGAACTGTGAATGCGCAAACCAACCCTTGGCAGAACATATCCATCGCGTCCGCCATCTCCAGC
AGCCGCACGCGGCGCATCTCGGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAAGATACC
AGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCAATGCTCACGCTGTACCTATCTC
AGTTCGGTGTACCTCGTTCGCTCCAAGCTGGGCTGTGTGCACGAACCCCCGTTCAGCCCGACC
GCTGCGCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGAGTTCTTG
AAGTGGTGGCCTAACTACGGCTACACTAGAAGGACAGTATTTGGTATCTGCGCTCTGCTGAAGC
CAGTTACCTTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGA
GATTATCAAAAAGGATCTTCACCTAGATCCTTTTAAATTAAAAATGAAGTTTTAAATCAATCTA
AAGTATATATGAGTAAACTTGGTCTGACAGTTACCAATGCTTAATCAGTGAGGCACCTATCTCA
GCGATCTGTCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCTCACCGGCTCC
AGATTTATCAGCAATAAACCAGCCAGCCAGAAGGGCCGAGCGCAGAAGTGGTCCTGCAACTTTA
TCCGCCTCCATCCAGTCTATTAATTGTTGCCGGGAAGCTAGAGTAAGTAGTTCGCCAGTTAATA
GTTTGCGCAACGTTGTTGCCATTGCTGCAGGCATCGTGGTGTCACGCTCGTCGTTTGGTATGGC
TTCATTCAGCTCCGGTTCCCAACGATCAAGGCGAGTTACATGATCCCCCATGTTGTGCAAAAAA
GCGGTTAGCTCCTTCGGTCCTCCGATCGTTGTCAGAAGTAAGTTGGCCGCAGTGTTATCACTCA
TGGTTATGGCAGCACTGCATAATTCTCTTACTGTCATGCCATCCGTAAGATGCTTTTCTGTGAC
TGGTGAGTACTCAACCAAGTCATTCTGAGAATAGTGTATGCGGCGACCGAGTTGCTCTTGCCCG
GCGTCAACACGGGATAATACCGCGCCACATAGCAGAACTTTAAAAGTGCTCATCATTGGAAAAC
GTTCTTCGGGGCGAAAACTCTCAAGGATCTTACCGCTGTTGAGATCCAGTTCGATGTAACCCAC
TCGTGCACCCAACTGATCTTCAGCATCTTTTACTTTCACCAGCGTTTCTGGGTGAGCAAAAACA
GGAAGGCAAAATGCCGCAAAAAAGGGAATAAGGGCGACACGGAAATGTTGAATACTCATACTCT
TCCTTTTTCAATATTATTGAAGCATTTATCAGGGTTATTGTCTCATGAGCGGATACATATTTGA
ATGTATTTAGAAAAATAAACAAATAGGGGTTCCGCGCACATTTCCCCGAAAAGTGCCACCTGAC
GTCTAAGAAACCATTATTATCATGACATTAACCTATAAAAATAGGCGTATCACGAGGCCCTTTC
GTCTTCAA
```

FIG. 4D

MORPHOLOGY & FLUORESCENCE OF PLE9 TRANSDUCED CELLS AT DAY 53

TRANSGENIC CIRCULATING ENDOTHELIAL CELLS

CROSS-REFERENCE TO RELATED APPLICATIONS

This application is a continuation of PCT/US99/28033, filed Nov. 24, 1999, which claims the benefit of the filing date of U.S. application Ser. No. 60/109,687, filed Nov. 24, 1998.

This invention was made with the support of NIH Grant No. HL 55174 (now HL 30160). The Government has certain rights in the invention.

BACKGROUND OF THE INVENTION

The endothelial cell participates in numerous functions of vascular physiology. Many factors, such as cytokines, can alter the surface of the endothelial cell and thereby modulate the role of the endothelium in coagulation, inflammation, vaso-regulation, and adhesion. See, for example, R. P. Hebbel et al., *J. Lab. Clin. Med.*, 129, 288 (1997); J. S. Pober, *Am. J. Path.*, 133, 426 (1988); E. J. Favaloro, *Inmmunol. Cell. Biol.*, 71, 571 (1993). The endothelial cell may also have a key role in the vascular pathology of sickle cell anemia, including the vaso-occlusions that cause acute painful crises. However, research in this area has been hindered by the inaccessibility of vascular endothelium in patients. For example, E. M. Levine et al. (U.S. Pat. No. 5,132,223) disclosed cloning and serial cultivation of adult human endothelial cells derived from brain-dead, but heart-beating cadaver organs. K. Gupta et al., *Exp. Cell. Res.*, 230, 244 (1997) reported the culture of microvascular endothelial cells derived from newborn human foreskin. Thus, circulating endothelial cells might provide useful material for the study of vascular pathologies, for gene therapy, and for biomedical engineering applications. In previous investigations increased numbers of circulating endothelial cells have been found in sickle cell anemia and other conditions associated with vascular injury, such as that due to cytomegalovirus infection, rickettsial infection, myocardial infarction, intravascular instrumentation, and endotoxinemia. See, for example, F. George et al., *Blood*, 80, Suppl: 12a, abstract (1992); E. Percivalle et al., *J. Clin. Invest.*, 92, 663 (1993), F. George et al., *Blood*, 82, 2109 (1993); C. A. Bouvier et al., *Thomb. Diath. Haemorrh. Suppl.*, 40, 163 (1970); F. George et al., *J. Immunol. Meth.*, 139, 65 (1991) and R. G. Gerrity et al., *Exp. Mol. Pathol.*, 24, 59 (1976).

However, in normal donors, there are only about 2–3 circulating endothelial cells per ml of blood; they have a quiescent phenotype, and about 50% of them are microvascular as evidenced by CD36 positivity. See, A. Solovey et al., *New Engl. J. Med.*, 337, 1584 (1997), who reported using the methodology of Gupta et al., cited above, to coculture viable circulating endothelial cells identified in the blood of patients with sickle cell anemia with primary microvascular endothelial cells (MVEC). T. Asahara et al., *Science*, 275, 964 (1997) isolated putative endothelial cell (EC) progenitors from human peripheral blood after $CD34^+$ enrichment by magnetic bead selection on the basis of cell surface antigen expression. The cells were cultured on fibronectin-coated wells in modified M-199 medium containing bovine brain extract and 20% fetal bovine serum. Q. Shi et al., *Blood*, 92, 362 (1998) characterized bone marrow-derived precursor endothelial cells by isolating $CD34^+$ cells derived from peripheral blood using murine anti-$CD34^+$ antibody binding followed by exposure to anti-mouse immunomagnetic beads. The cells were cultured in gelatin or fibronectin-coated plastic wells in M199 medium containing VEGF, FBS, bFGF and IGF.

However, due to the low concentration of CEC in blood, a need exists for a culture method and medium that will permit the rapid expansion of CEC from blood, without the attendant difficulties of isolation discussed above.

SUMMARY OF THE INVENTION

The present invention provides a process for expanding the population of endothelial cells (EC) present in an aliquot of peripheral mammalian blood, i.e., blood obtained from an animal or human patient. The process comprises culturing buffy coat mononuclear cells, which are readily obtained from peripheral mammalian blood. The buffy coat mononuclear cells are cultured in contact with a surface coated with collagen I, such as a coated plastic culture well, wall of a culture flask or bioreactor, in a culture medium containing an effective amount of vascular endothelial growth factor (VEGF), which medium is free of bovine brain extract. Optionally, the buffy coat mononuclear cells can thereafter be cultured in contact with a surface coated with fibronectin/gelatin. The medium can also comprise heparin and/or dextran sulfate, and other growth factors conventionally employed in endothelial cell culture media. The present method accomplishes the rapid and extensive expansion of the initial population of endothelial cells and any endothelial progenitor cells present in the population of buffy coat mononuclear cells. For example, the present method typically results in an outgrowth of endothelial cells that is at least a billion-fold greater than the 20–30 endothelial cells identifiable on culture day #2, when endothelial cells are first counted. The endothelial outgrowth includes the expansion of two populations. There is a limited expansion of the mature endothelial cells of vessel wall origin that are found in fresh blood, as well as a delayed, but greater, expansion of a rarer population of marrow-derived cells, e.g., endothelial progenitor cells or angioblasts, that are also found in fresh blood.

Unexpectedly, the cultured endothelial cells have been found to be amenable to cryopreservation in conventional cryopreservation media, followed by thawing and continued culture/expansion. The present method is thus more convenient and less complex than methods based on processing and culturing adult vessel human endothelial cells, as described, for example, in E. M. Levine et al. (U.S. Pat. No. 5,132,223). It does not comprise selection of subpopulations of EC-enriched hematopoietic cells using antibodies and/or magnetic bead technology.

The present invention also comprises an isolated, purified transgenic mammalian endothelial cell comprising a recombinant DNA sequence encoding at least one biologically active preselected protein or polypeptide, such as a Factor VIII protein, and optionally, a selectable marker gene or reporter gene. Preferably, the transgenic endothelial cell is prepared by stably transforming (transfecting/transducing) a population of circulating endothelial cells outgrown from blood in accord with the present method, with a vector comprising an isolated DNA sequence encoding the protein/polypeptide of interest, operably linked to a promoter functional in said endothelial cells.

A population of said transgenic cells can be formulated into a pharmaceutical composition and administered to a mammal, such as a human patient afflicted with hemophilia, preferably in combination with a pharmaceutically acceptable carrier. The carrier may be a liquid carrier (for example, a saline solution) or a solid carrier; e.g., an implant. In employing a liquid carrier, the engineered cells may be introduced, e.g., intravenously, sub-cutaneously, intramuscularly, intraperitoneally, intralesionally, and the like. The polypeptide, such as Factor VIII protein or proteins are expressed in situ, i.e., in the bloodstream of said mammal in an amount effective to treat (alleviate) said hemophilia. Since the transgenic endothelial cells will also migrate to the bone marrow, they are also useful for many aspects of gene therapy, apart from treating circulatory pathologies. Other uses of these transgenic EC, such as in biocompatibilization of implantable devices, diagnostics, and local drug delivery, are discussed hereinbelow.

Novel vectors useful for transforming the expanded circulating endothelial cells of the invention are also within the scope of the invention.

BRIEF DESCRIPTION OF THE DRAWINGS

FIG. 3 depicts the DNA sequence of HSQ/eGFP (SEQ ID NO:1). (HBFVIII/SQ/egfp) which comprises original HB with B-domain SQ insert based on Lind et al., *Eur. J. Biochem.*, 232; and p21 primer sequence containing eGFP protein sequence.

FIG. 4 shows the DNA sequence (SEQ ID NO:2) of HSQRENeo.

DETAILED DESCRIPTION OF THE INVENTION

Figure 1:
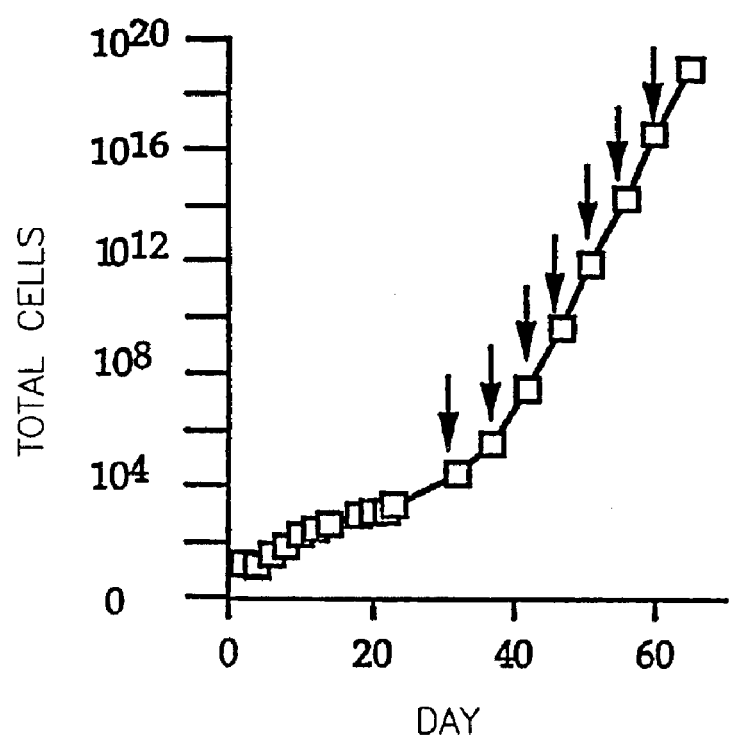
FIG. 1 is a graph plotting the outgrowth of endothelial cells in accord with the method of the invention. Arrows show times at which cultures were passaged. All data points are plotted as mean±SD. Data are shown for n=5 through culture passage 6, and n=4 for subsequent passages.

The endothelial cell culture medium used in the process of this invention comprises any of the media conventionally employed for the culture of this type of cell, as modified in accord with the present method, to include an effective amount of endothelial cell growth factor (ECG or VEGF), and to exclude bovine brain extract. The exclusion of bovine brain extract is advantageous both from a standpoint of consistency of formulation, and from a health standpoint, in that cells are not subjected to the risk of contamination with infectious agents (viruses, prions, etc.) which may be present in such extracts.

Preferably, the medium contains heparin, dextran sulfate or a combination thereof. These materials are described in detail in U.S. Pat. No. 5,132,223. Of the various basal endothelial cell growth media, EGM®-2 (Clonetics, Inc., San Diego, Calif.) is particularly preferred. It is based on CCMD®130 culture medium plus human epidermal growth factor (hEGF), human basic fibroblast growth factor (hFGF-B), human recombinant insulin-like growth factor (Long R3-IGF-1). FGF can be present at about 0.5–5 ng/ml, EGF can be present at about 0.5–10 ng/ml and IGF can be present at about 1–7.5 ng/ml of the culture medium.

The medium can also comprise hydrocortisone (0.1–2 µg/ml), heparin (1–20 µg/ml), gentamicin, amphotericin-B (0.1–0.5 mg/ml) and fetal bovine serum. Vascular endothelial growth factor (VEGF) is present at about 1–100 ng/ml, preferably about 5–25 ng/ml. It is included within this concentration range in some commercially available media or supplements or is available from Collaborative Research, Inc. VEGF can also be prepared as described by Maciag et al., *PNAS USA*, 76, 5674 (1979).

A medium that is effective to disperse and pre-wash the buffy coat mononuclear cells prior to culturing, has been described by K. Gupta et al., *Exp. Cell Res.*, 230, 244 (1997). This endothelial culture medium consists of MCDB 131 medium supplemented with 1 µg/ml hydrocortisone acetate, $5 \times 10^{-4}$ M bibutyryl cAMP, 1.6 nM L-glutamine, 100 U/ml penicillin, 100 U/ml streptomycin, 0.25 mg/ml amphotericin B, 0.004% heparin and 20% human male serum. VEGF (0.01–100 ng/ml) can also be added to this medium.

Circulating endothelial cells can be isolated from whole blood via isolation of the buffy coat mononuclear cells by methodologies well-known to the art. For example, see A. Solovey et al., *New Engl. J. Med.*, 337, 1584 (1997). Whole blood is anti-coagulated and diluted with a physiological salt solution containing EDTA and BSA. The diluted blood is layered onto Histopaque® 1077 (Sigma Chem. Co.) and centrifuged at ambient temperature. The buffy coat mononuclear cells are collected and washed by centrifuging with the medium described in K. Gupta et al., *Exp. Cell. Research*, 230, 244 (1977), described hereinabove, i.e., supplemented MCDB 131 medium.

The buffy coat mononuclear cells are resuspended in the endothelial cell culture medium (i.e., EGM®-2) and held in a suitable vessel having the walls thereof coated with collagen I. Type I collagen is commercially available from Sigma Chem. Co. (St. Louis, Mo.) and is obtainable from bovine Achilles tendon, calf skin, rat tail, and human placenta. See, for example, Niyiloizi et al., *J. Biol. Chem.*, 259, 14170 (1984). On day two of culture, unattached buffy coat mononuclear cells and cell debris are removed when the medium is changed, and the small number of adhered cells exhibit endothelial cell morphology, and stain positive with mAb P1H12.

Cultured cells were evaluated by inverted phase-contrast microscopy to confirm the characteristic cobblestone morphology of the endothelial cells and to examine for the presence of cells other than endothelial cells. Cells were also analyzed for von Willebrand factor (vWF) and CD36 expression by immunofluorescence and flow cytometry. The presence of cell surface CD36 has been used as a marker for human microvascular endothelial cells (HDMEC), as it has been shown that most MEC express CD36, but endothelial cells lining large vessels do not. Briefly, cells in suspension were fixed with paraformaldehyde, cytospun onto glass slides, washed, and incubated with either rabbit anti-human vWF (1:400 dilution) or anti-CD36 mAb FA6-152 (5 µg/ml) (Immunotech, Westbrook, Me.). Slides were then washed and incubated with secondary antibodies conjugated to rhodamine or fluorescein, washed, and viewed under a fluorescent microscope.

To identify endothelial cells, the antibody P1H12 was also used. This murine IgG1 monoclonal antibody was obtained by immunizing mice with HUVEC, generating a hybridoma line, and separating IgG from supernatants of hybridoma cell cultures with a protein G column. For some studies, fluorescein isothiocyanate-labeled P1H12 was used, prepared with the Fluoro Tag FITC Conjugation kit (Sigma).

P1H12 reacts specifically with endothelial cells in blood. It stains primary HUVEC and MVEC cultures and the endothelial cells of all vessels in frozen sections of human skin, intestine, ovary, tonsil, lymph node, lung, and kidney. It does not stain any other type of cell in those tissues. It does not stain carcinoma cell lines HT-29 and COLO205, melanoma cells lines A-375 and M21, the T-cell lines Jurkat and HuT78, fibroblasts, HL-60 or Chinese-hamster-ovary cells, or Epstein-Barr virus-transformed B-cell lines. It does not stain monocytes, granulocytes, red cells, platelets, T cells, or B cells from marrow or peripheral blood; nor does it react with marrow megakaryocytes or the megakaryoblast line HU3. The peripheral blood cells that do stain with P1H12 are also positive for both von Willebrand factor and thrombomodulin (the combined expression of which is limited to endothelium), and they stain for flt and flk (receptors for the endothelial-specific vascular endothelial growth factor). Subgroups of P1H12-positive blood cells also stain for CD34 and two endothelial-specific activation markers (VCAM and E-selectin).

After good EC growth is obtained, preferably after about $10^3$-fold expansion, or at 15–25 days, the cells are trypsinized and isolated from the supernatant by centrifugation. The cells are then suspended in the initial culture medium in a flask coated with fibronectin/gelatin for continued culture. Clones can be derived from secondary cultures and seeded at about 10 cells/cm$^2$ of flask surface. The clones are then serially propagated in the culture medium.

It was also found that EC cultured in accord with the present method can be cryopreserved and then thawed and returned to culture without significant loss of their capacity to proliferate. To cryopreserve the cells, the cultured cells can be detached as described hereinabove and resuspended in suitable cryopreservation medium, i.e., containing a cryopreservation agent such as sugar(s), BSA, dimethylsulfoxide (DMSO), glycerol, glycerol esters and the like.

Cryopreservation of hematopoietic cells, such as bone marrow and peripheral blood fractions enriched in progenitor stem cells, has become standard clinical practice for autologous bone marrow transplantation (Areman et al., *Bone Marrow and Stem Cell Processing: A Manual of Current Techniques*, F. A. Davis, Philadelphia, Pa., 1st edition (1992)). Two basic techniques are used to cryopreserve hematopoietic cells. The most commonly used technique in clinical laboratories, uses tissue culture medium combined with 95% fetal calf serum ("FCS"), and 5 v/v % dimethylsulfoxide ("DMSO"). After suspension in the cryopreservation medium, the cells are placed on ice for about 5 minutes, then at −70° C. overnight and finally in liquid nitrogen. This technique was developed in the early 1960s by Ashwood-Smith (see Sputtek et al., *Clinical Applications of Cryobiology*, Chapter 5, 127–147 (CRC Press, Boca Raton, Fla., 1991)), and has been the predominant technique used in clinical practice. In early 1983, Stiff and colleagues developed a modified method for the preservation of stem cells (Stiff et al., *Cryobiology*, 20, 17–24 (1983)). In this method, the concentration of DMSO was reduced to 5% and an additional cryoprotective agent, hydroxyethyl starch ("HES"), was added to the solution. The cells could be frozen using a controlled rate freezer or in a mechanical freezer at −80° C.

In present clinical practice, the base of most cryopreservation solutions is a tissue culture medium, potentially containing many different components. Typical tissue culture media include RPMI 1640, IMDM, AIM-5, X-VIVO 10, or α MEM.

The cell suspension is then frozen, i.e., at liquid nitrogen temperatures in a suitable container and stored until needed. The frozen suspension is then thawed, by immersing the container in a warm water bath and culturing can be resumed. The resulting EC growth is similar to that of cells that were not subjected to cryopreservation.

The cultured EC may also be used in gene therapy wherein a gene producing a protein polypeptide, enzyme or other product is inserted into the DNA of the EC. The transgenic EC are then administered to a mammal, e.g., by infusion into a patient's bloodstream. See, for example, B. P. Luskey et al., *Annals. N.Y. Acad. Sci.*, 612, 398 (1990), B. A. Naughton et al. (U.S. Pat. No. 4,721,096), and Anderson et al. (U.S. Pat. No. 5,399,346).

The gene carried by the EC can be any gene which allows the blood cells to exert a therapeutic effect that they would not ordinarily have, such as a gene encoding a clotting factor, such as Factor VIII, useful in the treatment of hemophilia. The gene can encode one or more products having therapeutic effects. Examples of suitable genes include those that encode cytokines such as TNF, interleukins (interleukins 1–12), interferons (α, β, γ-interferons), T-cell receptor proteins and Fe receptors for antigen-binding domains of antibodies, such as immunoglobulins.

Additional examples of suitable genes include genes that modify EC to "target" a site in the body to which the blood cells would not ordinarily "target," thereby making possible the use of the blood cell's therapeutic properties at that site. In this fashion, blood cells such as TIL can be modified, for example, by introducing a Fab portion of a monoclonal antibody into the cells, thereby enabling the cells to recognize a chosen antigen. Likewise, blood cells having therapeutic properties can be used to target, for example, a tumor, that the blood cells would not normally target. Other genes useful in cancer therapy can be used to encode chemotactic factors which cause an inflammatory response at a specific site, thereby having a therapeutic effect. Other examples of suitable genes include genes encoding soluble CD4 which is used in the treatment of HIV infection and genes encoding α-antitrypsin, which is useful in the treatment of emphysema caused by α-antitrypsin deficiency, or genes encoding factors which promote bone growth such as bone morphogenic proteins (BMPs) or other factors in the BMP pathway.

The gene therapy of the present invention is useful in the treatment of a variety of diseases including but not limited to adenosine deaminase deficiency, sickle cell anemia, thalassemia, hemophilia, diabetes, α-antitrypsin deficiency, brain disorders such as Alzheimer's disease, and other illnesses such as growth disorders and heart diseases, for example, those caused by alterations in the way cholesterol is metabolized and defects for the immune system, as well as to repair bone fractures or treat or prevent osteoporosis.

In still another embodiment, there is provided a method of detecting the presence of human CEC present in a patient, comprising: (i) inserting into an expanded population of human CEC removed from the patient a DNA segment encoding the detectable marker under conditions such that the marker is expressed in the CEC; (ii) introducing cells resulting from step (i) into the patient; (iii) removing from the patient an aliquot of tissue (which can be, for example, normal tissue, cancerous tissue, vascular tissue, blood, lymph nodes, etc.) including cells resulting from step (ii) and their progeny; and (iv) detecting or determining the quantity of the cells resulting from step (ii) and their progeny, in said aliquot.

To effect gene therapy with a substantially pure population of human EC, the following general method may be used to insert a gene into these EC. For a review of transformation methodologies, see Friedmann, *Science,* 244, 1275 (1989) and *Lancet,* Jun. 4, 1988, p. 1271. In order to introduce a normal structural gene, to correct a genetic error, a gene can first be isolated from the cells of a donor. The cells may be isolated from tissue(s), blood or other body fluids. To find a gene coding for the defective protein, DNA from the donor cell is isolated and cleaved by enzymatic digestion into segments of varying length by means known to those skilled in the art. The segments of DNA then may be inserted individually into vectors containing the appropriate regulatory sequences for expression of a gene product. The vectors then can be screened by conventional means such as Northern blotting, if the sequence for the normal gene is known, or the expression product can be screened by Western blotting.

Alternatively, if the DNA sequence of the desired gene or the sequence of the normal protein is known, the gene can be made by synthetic methods such as by using a DNA synthesizer (Applied Biosystems). In any case, the method of isolation or construction of the gene sequence can yield a "normal" gene that codes for the desired gene product. Once isolated, a functional structural gene, such as a DNA sequence coding for a factor VIII protein, human factor VIII, porcine factor VIII and the like can be modified for expression in vivo by linkage to suitable control regions, such as promoters. Hybrid or modified genes can also be constructed, such as DNA sequences encoding factor VIII molecules, modified to reduce their antigenicity and immunogenicity. DNA methods can be used to substitute elements of animal factor VIII for the corresponding elements of human factor VIII, resulting in hybrid human/animal factor VIII molecules. The preparation of transformation vectors comprising DNA sequences encoding chimeric hybrid Factor VIII molecules is disclosed in Lollar et al. (U.S. Pat. No. 5,744,446). DNA methods may also be used to substitute amino acid residues at selected sites, such as epitopes, to yield factor VIII constructs having improved therapeutic attributes such as reduced antigenicity or immunogenicity or greater potency in comparison to unmodified human factor VIII.

In a preferred embodiment, a hybrid human/porcine cDNA encoding factor VIII, in which the porcine sequence encodes a domain or part domain, such as the A2 domain or part domain, is inserted in a mammalian expression vector, such as ReNeo, to form a hybrid factor VIII construct. Preliminary characterization of the hybrid factor VIII is accomplished by insertion of the hybrid cDNA into the ReNeo mammalian expression vector and transient expression of the hybrid protein in COS-7 cells. A determination of whether active hybrid protein is expressed can then be made. The expression vector construct is used further to stably transfect cells in culture, such as baby hamster kidney cells, using methods that are routine in the art, such as liposome-mediated transfection (Lipofectin™, Life Technologies, Inc.). Expression of recombinant hybrid factor VIII protein can be confirmed, for example, by sequencing, Northern and Western blotting, or polymerase chain reaction (PCR). Hybrid factor VIII protein in the culture media in which the transfected cells stably expressing the protein are maintained can be precipitated, pelleted, washed, and resuspended in an appropriate buffer, and the recombinant hybrid factor VIII protein purified by standard techniques, including immunoaffinity chromatography using, for example, monoclonal anti-A2-Sepharose™.

In a further embodiment, the hybrid factor VIII comprising subunit, domain, or amino acid sequence substitutions is expressed as a fusion protein from a recombinant molecule in which a sequence encoding a protein or peptide that enhances, for example, stability, secretion, detection, isolation, or the like is inserted adjacent to the factor VIII encoding sequence. Established protocols for use of homologous or heterologous species expression control sequences including, for example, promoters, operators, and regulators, in the preparation of fusion proteins are known and routinely used in the art. See *Current Protocols in Molecular Biology* (Ausubel, F. M. et al., eds.), Wiley Interscience, New York.

The purified hybrid factor VIII or fragment thereof can be assayed for coagulation activity by standard assays including, for example, the plasma-free factor VIII assay, the one-stage clotting assay, and the enzyme-linked immunosorbent assay using purified recombinant human factor VIII as a standard. Antigenicity and immunogenicity of factor VIII constructs may be tested in vitro using the standard Bethesda inhibitor assay, or in vivo using a knockout hemophilic mouse model.

Other vectors, including both plasmid and eukaryotic viral vectors, may be used to express a recombinant gene construct in eukaryotic cells depending on the preference and judgment of the skilled practitioner. Other vectors and expression systems, including bacterial, yeast, and insect cell systems, can be used but are not preferred due to differences in, or lack of, glycosylation.

The same methods employed for preparing hybrid human/ porcine factor VIII having subunit, domain, or amino acid sequence substitution can be used to prepare other recombinant hybrid factor VIII protein and fragments thereof and the nucleic acid sequences encoding these hybrids, such as human/non-human, non-porcine mammalian or animal/ animal. As used herein the term "Factor VIII protein" includes any of these materials that are biologically active as determined by the assays listed above, i.e., that possess coagulation activity when assayed in vitro. The murine and part of the porcine factor VIII cDNA have been cloned. Factor VIII sequences of other species for use in preparing a hybrid human/animal or animal/animal factor VIII molecule can be obtained using the known human and porcine DNA sequences as a starting point. Other techniques that can be employed include PCR amplification methods with animal tissue DNA, and use of a cDNA library from the animal to clone the factor VIII sequence.

Once the DNA containing the gene is prepared, the DNA can be inserted into the population of EC isolated and expanded as above. The DNA can be inserted by 1) physical methods such as coprecipitation with calcium phosphate, electroporation, lipofection or microinjection (e.g., U.S. Pat. No. 4,873,191), and/or by 2) the use of viral vectors such as adenoviruses, if the DNA is less than approximately 7–8 kB, or retroviruses for longer segments of DNA. In the latter case, the DNA of the retrovirus is cut with a restriction enzyme and the human DNA containing the desired sequence is inserted and ligated. The retrovirus containing the insertion then is transfected into the EC. The EC then can be assayed for production of the desired protein. See, e.g., U.S. Pat. Nos. 4,902,783 and 5,681,746.

In general, molecular DNA cloning methods are well known in the art and are not limiting in the practice of this invention. For a further description of similar methods, see Friedmann, *Science,* 244, 1275 (1989) and *Molecular Cloning: A Laboratory Manual* (2nd ed.), Cold Spring Harbor Laboratory Press, Sambrook, Fritsch and Maniatis eds. (1989).

Transgenic, i.e., transduced, endothelial cells stably incorporating and expressing heterologous DNA or RNA and therapeutic uses therefore, are described in Mulligan et al. (U.S. Pat. No. 5,674,722). In particular, retroviral vectors have been used to stably transduce endothelial cells with genetic material which includes genetic material encoding a polypeptide or protein of interest not normally expressed at biologically or therapeutically significant levels in endothelial cells. The genetic material introduced in this manner can also include genetic material encoding a dominant selectable marker, such as antibiotic or herbicide resistance. Genetic material including DNA encoding a polypeptide of interest alone, such as a Factor VIII protein, or DNA encoding a polypeptide of interest and a dominant selectable marker can be introduced into cultured endothelial cells. Expression of these genes by the endothelial cells into which they have been incorporated (i.e., endothelial cells transduced by the use of retroviral vectors) has also been demonstrated.

Endothelial cells transduced in vitro with the genetic material can then be transplanted using one of a variety of known methods. Such methods include, but are not limited to, the transplantation of synthetic vessels or prosthetic valves lined with transduced endothelial cells or the transplantation of a device or matrix designed to house transduced endothelial cells.

To administer the EC containing the desired gene, the cells may simply be introduced into the bloodstream of the patient by conventional means, such as of intravenous infusion over a period of time.

Endothelial cells which have been transduced in vitro are particularly useful for improving prosthetic implants (e.g., vessels made of synthetic materials such as Dacron®, Gortex® and other plastics or metal-plastic laminates), including shunts, stents and grafts, which are used in vascular reconstructive surgery. For example, prosthetic arterial grafts are often used to replace diseased arteries which perfuse vital organs or limbs. However, the currently available grafts are usually made of synthetic material and are subject to many complications, the worst of which is a high rate of thrombosis or occlusion. Animal studies suggest that lining the graft with autologous endothelial cells prior to implantation may decrease, but not prevent, graft reocclusion with its attendant morbid consequences.

However, endothelial cells can be modified according to the method of the present invention in a way that improves their performance in the context of an implanted graft or provides a means for local drug delivery. Examples include local delivery to the interior of the lumen of antirestenotic, antiproliferative, or thrombolytic agents to prevent intraluminal clot formation, secretion of an inhibitor of smooth muscle proliferation to prevent luminal stenosis due to smooth muscle hypertrophy, and expression and/or secretion of an endothelial cell mitogen or autocrine factor to stimulate endothelial cell proliferation and improve the extent or duration of the endothelial cell lining of the graft lumen. The latter agents are termed "biocompatibilization" agents (polypeptides or proteins).

For a similar application, endothelial cells of the present invention can also be used to cover the surface of prosthetic heart valves to decrease the risk of the formation of emboli by making the valve surface less thrombogenic.

Endothelial cells transduced by the method of the subject invention or a vascular implant lined with transduced endothelial cells can also be used to provide constitutive synthesis and delivery of polypeptides or proteins, which are useful in prevention or treatment of disease, such as Factor VIII proteins, to treat hemophilia. In this way, the polypeptide is secreted directly into the bloodstream of the individual, from circulating cells, over an extended period of time. Currently available methods, in contrast, involve parenteral administration of the desired polypeptide.

In addition, there is no need for extensive purification of the polypeptide before it is administered to an individual, as is generally necessary with an isolated polypeptide (e.g., insulin). Endothelial cells modified according to the present invention produce the polypeptide hormone as it would normally be produced.

Another advantage to the use of genetically engineered endothelial cells is that one can target the delivery of therapeutic levels of a secreted product to a specific organ or limb. For example, a vascular implant lined with endothelial cells transduced in vitro can be grafted into a specific organ or limb; or the endothelial cells of a particular limb, organ or vessel can be transduced in vivo. The secreted product of the transduced endothelial cells will be delivered in high concentrations to the perfused tissue, thereby achieving a desired effect to a targeted anatomical location. This product will then be diluted to nontherapeutic levels in the venous circulation during its return to the heart.

Another important advantage of the delivery system of this invention is that because it is a continuous delivery system, the short half lives of hormone polypeptides is not a limitation. For example, the half life of human growth hormone (HGH) is approximately 19 minutes and parathyroid hormone, approximately 2½ to 5 minutes.

The invention will be further described by reference to the following detailed examples.

EXAMPLE 1

Culture of Endothelial Cells from Peripheral Blood

One hundred ml of fresh venous blood anti-coagulated with either heparin or citrate was diluted 1:2 with Hanks' Balanced Salt Solution (HBSS) containing 1 mM EDTA and 0.5% bovine serum albumin, carefully layered on an equal volume of Histopaque®-1077 (Sigma Chemical Co.) without disruption of the interface, and centrifuged at 400×G for 30 minutes at room temperature. The layer containing the mononuclear cells was collected, and the cells were washed 3 times by centrifuging at 250×G for 10 minutes, using the previously described MEC media (Gupta et al., *Exp. Cell Res.*, 230, 244–251 (1997)) modified to contain 10% human male serum, to exclude the ECGS and comprising 1 µg/ml hydrocortisone. Washing with this culture medium is preferred over washing with buffer because the medium maintains higher levels of cell viability.

The buffy coat mononuclear cells were resuspended in EGM®-2 medium (Clonetics), and all buffy coat mononuclear cells from 100 ml of starting blood were placed into one well of a 6-well plate coated with collagen I (Becton-Dickinson). This is defined as day #1, on which the plate is placed into an incubator at a controlled temperature (37° C.) and humidified environment (5% $CO_2$). The EGM®-2 medium is changed daily. On day #2, most of the buffy coat mononuclear cells have remained unattached and they and cell debris were removed at the time of culture medium change. This left on the bottom of the culture well a small number of cells that have typical endothelial cell morphology and which stain positively with anti-endothelial monoclonal antibody P1H12. Typically, there were about 20–30 such cells identifiable on day #2, along with 100–200 other mononuclear cells.

After good cell growth was established (typically at about 20 days, when cells may or may not be confluent), they are passed into a fibronectin/gelatin-coated T25 flask, and then into fibronectin/gelatin-coated T75 flasks. To pass the cells, the wells are washed twice with calcium-free HBSS and then once with 0.5×trypsin (i.e., 50% of the concentration for the Gibco BRL trypsin product recommended for cell lifting, because it is less harsh than the full-strength product) plus 1 mM EDTA. Cells detach after 2 minutes. Trypsin is neutralized by adding an equal volume of human serum or MEC media containing 20% human serum. Cells were collected from the solution by centrifugation at 250×G for 5 minutes, and resuspended in EGM®-2 medium for continued culture.

FIG. 1 is plot of the outgrowth of endothelial cells expanded using this method. The mean±SD of five different culture experiments using five different blood donors was plotted up until culture passage 5, after which four different cultures were plotted. Error bars are not evident on the graph because of the high reproducibility of the method. As shown, the method of the invention can result in an outgrowth, and a $10^{18}$ fold expansion, of endothelial cells far greater than the 20–30 endothelial cells identifiable on culture day #2 (the day the unattached mononuclear cells and cell debris from the buffy coat are removed and any EC can be first identified).

It should be noted that this fold expansion is not a maximal expansion. It is just the degree of expansion allowed before cells are used for further experiments. The maximal cap (if any) in expandability of these cells, therefore, has not yet been established or reached in these experiments.

The outgrowth cells have the characteristics of quiescent, microvascular EC. They have typical "cobblestone" endothelial morphology; they exhibit positive expression for von Willebrand Factor, P1H12 antigen, ICAM1, $\alpha_V\beta_3$, $\beta_2$-microglobulin, thrombomodulin, flk-1 (a VEGF receptor), and CD34; they are uniformly CD36-positive; they take up acetylated-LDL; they do not constitutively express tissue factor or VCAM, but do express both upon appropriate stimulation.

EXAMPLE 2

Cyropreservation of Cultured Endothelial Cells

Vigorous EC outgrowth can be obtained even after cryopreservation. This is important because the utility of the present method is greater if cultured EC can be cryopreserved for later use.

To show this, EC were cryopreserved after their outgrowth had reached the capacity of two T75 flasks. To do this, the cells were detached as above and washed twice with HBSS. Cells were resuspended in 100% fetal calf serum at a concentration of one-million cells per 950 μl serum, and then 50 μl dimethylsulfoxide was added. The suspension was mixed quickly and placed on ice for 5 minutes. Afterward, the cells were stored at −70° C. overnight, and they were then transferred to liquid nitrogen.

After six weeks of storage, the cells were thawed and one million cells were plated onto T75 flask with excess (20 ml) of EGM®-2 medium. Medium was changed again four hours after initial plating. The cells were then grown as in Example 1.

Figure 2:
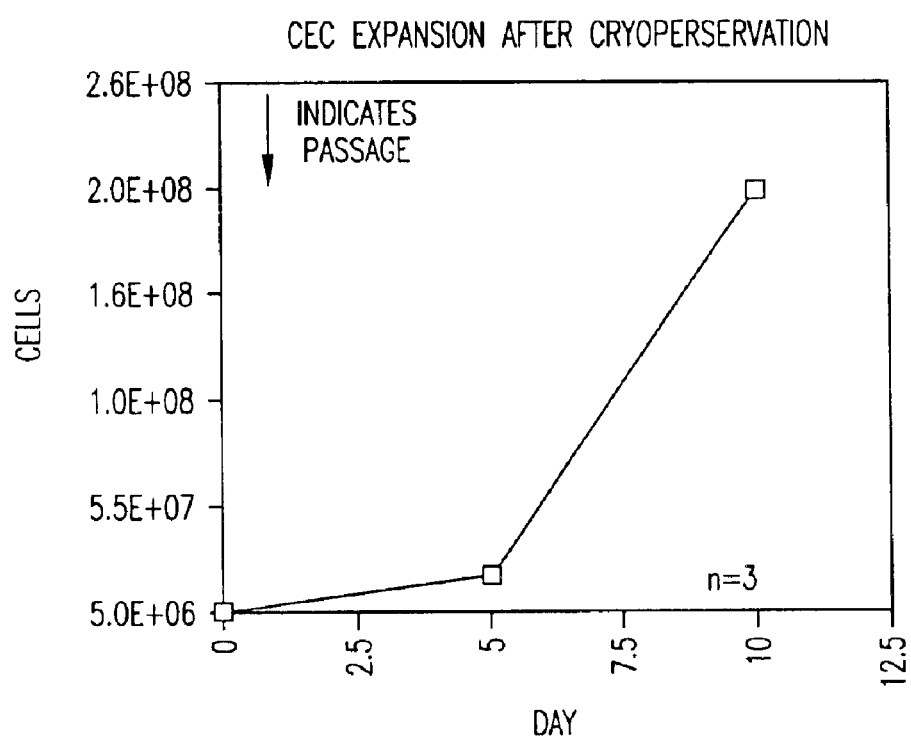
FIG. 2 is a graph plotting the outgrowth of endothelial cells that were subjected to cryopreservation.

The resulting growth is similar to that of EC that were not subjected to cryopreservation, as shown in FIG. 2. Again, data are shown as mean±SD for three experiments. Cell count at origin indicates the number of cells thawed and started with. These data suggest that the endothelial outgrowth cells expanded from blood resume their vigorous growth rate after cryopreservation.

EXAMPLE 3

Study of Origin of CEC in Blood

The origin of the CEC identifiable in fresh blood is not known, nor is the relationship between CEC and the endothelial outgrowth from cultured blood. To answer this, 4 adults were studied who had undergone allogeneic marrow transplantation (for malignancy) 5–20 months earlier using opposite-gender donors (three female donors to three male recipients and one male donor to one female recipient). All 4 subjects are disease-free and have peripheral blood and/or marrow aspirates that are 100% donor by RFLP; two also had marrow cytogenetics showing 100% donor.

The CEC in fresh blood, plus the peripheral blood endothelial outgrowth from buffy coat mononuclear cells cultured with endothelial growth factors was studied using the culture conditions of Ex. 1. MAb P1H12 was used to identify cells as being endothelial, and fluorescence in situ hybridization was used to identify cells as having XX or XY genotype.

CEC in fresh blood were almost exclusively of recipient genotype (95, 100, 100, 88%), arguing for their origin from the vessel wall. However, the blood endothelial outgrowth at 26–28 days (after 100-fold expansion) in culture was mostly donor genotype (82, 86, 77, 85%), revealing predominant origination from a marrow-derived cell. Remarkably, endothelial outgrowth at only 9 days (after 5-fold expansion) in contemporaneous culture was still largely recipient genotype (78, 88%). These data indicate that the CEC detected in fresh blood are derived from vessel wall and have some, but limited, expansion potential. Conversely, blood contains transplantable marrow-derived cells that take longer to expand but have greater proliferative potential. Thus, the CEC comprise a more mature and differentiated cell population, while there also are circulating marrow-derived endothelial-generating cells that comprise a more primitive progenitor population (putative angioblasts).

EXAMPLE 4

Transfection of CEC with Factor VIII Expression Vectors

Endothelial cells were expanded from blood, as described in Example 1. For these transfection experiments, they were used after 4–5 passages. They were plated in a 6 well plate at density of $2\times10^5$/well, and allowed to attach overnight. Then, cells in different wells were transfected by lipofection with one of four vectors as summarized in Table 1, below.

TABLE 1

| Plasmid Vectors for CEC Transfection |
| --- |
| A. Two vectors from Octagen with B-domainless FVIII replaced with green fluorescent protein (GFP):<br>#1    HSQ/eGFP/ReNeo<br>#2    HSQ/eGFP/CP |
| B. Control vector from Octagen with GFP but no factor VIII:<br>#3    pEGFP-N1 |
| C. Vector constructed at University of Minnesota, Department of Medicine with the FVIII/GFP from Octagen inserted between XhoI and NotI sites in commercial vector pcDNA3.1 (-):<br>#4    pcHSQ/eGFP |

All the transfection vectors contain the neomycin resistance gene (ReNeo) as a selection marker.

Vectors 1, 2 and 4 contain an HSQ/eGFP insert which codes for a fVIII-dGFP fusion protein. This insert comprises DNA that codes in order of sequence, 1) the human fVIII human activation peptide, 2) the human fVIII A1 domain, 3) the human fVIII A2 domain, 4) the first five amino acids of the SQ B domain linker peptide, 5) the enhanced green fluorescent protein (eGFP), 6) the last nine amino acids of the SQ linker peptide, 7) the human fVIII light chain activation peptide, 8) the human fVIII A3 domain, 9) the human fVIII C1 domain, and 10) the human fVIII C2 domain.

The DNA sequence of HSQ/eGFP is depicted in FIG. 3 (SEQ ID NO:1). The DNA sequence contains 5094 bases, encoding the peptides listed on Table 2.

TABLE 2

HSQ/eGFP Peptides SEQ ID NO: 1

| | |
|---|---|
| 1–57 | signal peptide |
| 58–1173 | A1 domain |
| 1174–2274 | A2 domain |
| 2275–2292 | SQ sequence (first part) |
| 2293–3012 | eGFP sequence |
| 3013–3039 | SQ sequence (second part) |
| 3040–3162 | light chain activation peptide |
| 3163–4152 | A3 domain |
| 4153–4611 | C1 domain |
| 4612–5091 | C2 domain |
| 5092–5094 | stop codon |

ReNeo is a mammalian expression vector (non-proprietary). The second plasmid, HSQ/eGFP/CP, contained the same FVIII construct but the vector is the same one used to express eGFP (see below). The eGFP protein was removed from p-EGFP-N1 and replaced with the HSQ/eGFP construct. The third plasmid is p-EGFP-N1 from Clontech, which expresses only eGFP.

The transfection protocol was based on the instructions supplied by Life Technologies Co. with the lipofectamine. Briefly, 2 micrograms of plasmid DNA was mixed gently with 15 microliters of lipofectamine in 200 microliters of E-STIM® basal medium (Becton Dickinson) without antibiotics. The mixture was allowed to stand at room temperature for 30 minutes. Expanded endothelial cells in 6-well plates were washed twice with E-STIM® basal medium before adding the DNA-liposome complex. Dropwise, 1.8 ml of E-STIM® was added to the DNA-liposome complex, then the mixture was overlaid on the endothelial cells. After 5 hours incubation, the DNA-liposome mixture was replaced with the endothelial culture medium of Example 1. Then, 2 days after transfection, the cells from one culture well were subcultured into one 10 cm dish in endothelial culture medium containing 50–100 $\mu$g/ml of Geneticin (Life Technologies Co.). This selection medium was changed every other day.

Transfection of endothelial cells derived from the blood of two donors has been accomplished to date. The number of endothelial colonies (derived from the transfection of greater than $2 \times 10^5$ cells) was checked on day 20 in selection medium for two donors, as shown on Table 3.

TABLE 3

Number of Colonies After 20 Days in Selection Medium

| Vector # | Donor 1 | Donor 2 |
|---|---|---|
| 1 | 3 | 9 |
| 2 | 2 | 8 |
| 3 | 4 | 7 |
| 4 | 1 | 8 |

On day 20, fluorescence microscopy showed all selected colonies to be positive for green fluorescent protein (GFP). On day 20, the colonies were pooled and transferred to the regular endothelial growth condition.

In the past, many basic and applied studies had to be performed on endothelial cells from other animal species because existing culture techniques permitted only restricted proliferation of human endothelial cells. The present method accomplishes at least a $10^{18}$-fold expansion of circulating human EC. This method will permit peripheral blood from living donors to be used for the generation of large numbers of cultured endothelial cells. Thus, problems of human pathology involving the endothelium now can be approached directly by employing a human endothelial cell model. In addition, expanded mammalian EC should prove valuable for various clinical applications, such as in vitro testing of vasoactive agents, the coating of artificial graft materials and gene therapy designed to treat vascular pathologies and genetic disorders, for local drug delivery and enhanced biocompatibility.

EXAMPLE 5

Use of Endothelial Cell Culture Methodology in Disease Diagnostics

Currently, there is no direct or non-invasive method to examine a patient's endothelium to assess it for either acquired or genetic defects that contribute to disease. A 25 year old male patient had been evaluated for the presence of a hypercoagulability disorder. The patient had a history of multiple thromboses, and a family history suggesting a familial pre-disposition to thrombosis. No positive diagnosis was obtained after extensive evaluation for known genetic and predisposing causes. Therefore, the patient was evaluated for a defect in thrombomodulin. Thrombomodulin is an enzyme that is expressed on the endothelial cell surface and is an anti-thrombotic defense. A patient having a mutation in thrombomodulin that leads to poor function would have an increased risk for thrombosis.

Endothelial cells were expanded from the blood of the patient and three normal control donors using the present method. Thrombomodulin activity was assessed in a standard biochemical assay. Briefly, a known number of endothelial cells is incubated with bovine protein C (100 $\mu$L per well of a 1 $\mu$M solution) and human recombinant thrombin (10 $\mu$L of 10 nM). It is incubated at 37° C. for 2.5 hours. The reaction is terminated by adding EDTA and I-2581 (Chromogenix AB, Molndal, Sweden), and the chromatographic substrate S-2366 (DiaPharma Group, Inc., Franklin, Ohio) is added. Supernatant absorbance is read at 405 nM.

The results are given in OD units per minute per 50,000 endothelial cells. The value for 18 samples from the three normal donors was 53±7, while the value for six samples from the patient was 41±5, a significant difference (p=0.0034). Thus, the expanded endothelial cells from the patient had a significantly lower thrombomodulin activity than those of control patients. Therefore, a genetic mutation in thrombomodulin resulting in a thrombomodulin deficiency may be the underlying basis for this patient's disorder. Molecular biological analyses are employed to confirm the genetic basis for the thrombomodulin deficiency.

EXAMPLE 6

Stable Transfection, Selection and Expansion

The plasmid pLE (Clontech), which contains sequence for enhanced green fluorescent protein (eGFP), was transfected into line PA317. Virus from one of the resulting cloned transfectants, pLE9, was employed to infect endothelial cells.

A culture of blood buffy coat mononuclear cells was set up according to the method of the invention. When cells had reached passage 4 and about a $10^6$ fold expansion, they were seeded at $10^5$ cells/dish, with the 10 cm dishes coated with 6 microgram/cm$^2$ of type 1 collagen and 250 microgram/dish of fibronectin in 1% gelatin. After two days of growth, the cells were exposed to conditioned medium from the packaging cell line in combination with 4 microgram/ml of polybrene to dishes that were 70% confluent. After three days exposure, cells were split 1:2 into a 10 cm dish (coated as above), and new culture medium added. Then they were subjected to selection in media containing G418 for 19 days.

Figure 5A:
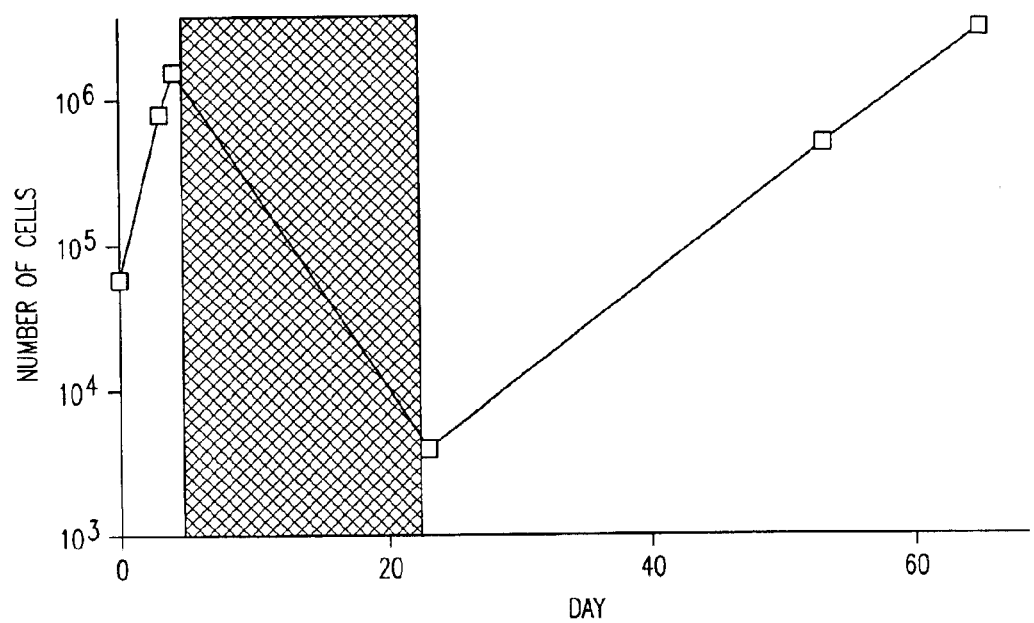
FIG. 5A shows the results of G418 selection of outgrowth endothelial cells stably transfected with a vector encoding eGFP.
Figure 5B:
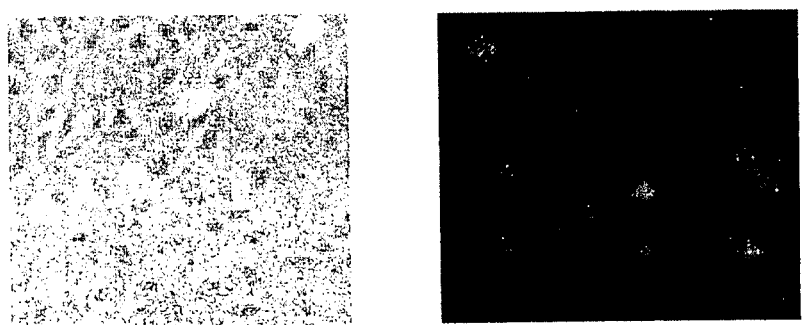
FIG. 5B shows the morphology (left) and fluorescence (right) of PLE9 transduced cells at day 53.

As shown in FIG. 5, cultured endothelial cells prepared according to the method of the invention can survive chemical selection and be expanded thereafter, and be stably transfected to express a foreign (non-selected) gene. Moreover, the outgrowth cells have preserved normal endothelial cell morphology.

EXAMPLE 7

Transfection of CEC with Human Factor VIII (hFVIII) Expression Vectors Materials and Methods Transfection Ten cm dishes and T75 flasks were coated with 6 μg/ml of type I collagen and 50 μg/ml of fibronectin. Passage 4 or 5 outgrowth endothelial cells were obtained as described in Example 1. They were seeded into the dish or flasks and allowed to grow to 40% confluence. Then the cells were transfected with hFVIII vectors (Table 4) using transfection reagent Fugene6 (Roche Molecular Biochemicals) following the manufacturer's protocol. Briefly, Fugene6 was added to each vector at a ratio of 2.5:1. Ten μg of DNA was used for transfection of cells in 10 cm dishes; and 15 μg of DNA was used for cells in T75 flasks.

The Fugene6-DNA mixture was added to the cells in media containing 10% human serum and incubated for 3 days. Cells reached 100% confluence after 3 days.

TABLE 4

Plasmid Vectors pTracerHSQ: has HSQ (the B-domainless hFVIII without the eGFP insert) cloned into pTracer-CMV (Invitrogen)
pcF8G: has HSQ/eGFP (eGFP replaces the B domain of hFVIII) cloned into plasmid pCDNA 3.1 (Invitrogen)
pcHSQ: has HSQ cloned into plasmid pCDNA 3.1 (Invitrogen)
pTracerCMV: obtained from Invitrogen
HSQ/GFP/ReNeo: has HSQ/eGFP cloned into pRENeo (Biogen)

Transient Expression

At the end of 3 days, the conditioned media from T75 flasks were collected and centrifuged. The presence of hFVIII in the supernatant was detected using an ELISA kit (American Diagnostics). Cells from T75 flask were harvested, lysed and processed (RT-PCR, Titan One Tube RT-PCR System, Roche Molecular Biochemicals) for detection of hFVIII mRNA. A reverse transcriptase reaction was conducted at 50° C. for 45 minutes, then the samples were subject to 94° C., for 2 minutes; 10 cycles of 94° C. for 30 seconds, 55° C. for 30 seconds, and 72° C. for 1 minute; 20 cycles of 94° C. for 30 seconds, 55° C. for 30 seconds, and 72° C. for 1 minute, plus cycle elongation of 5 seconds for each cycle elongation at 72° C. for 7 minutes. The primer pair employed was hFVIIIC-S (5' GCC CTT TTC TTG GAT CAA GGT GG3'; SEQ ID NO: 3) and hFVIIIC-AS (5' CTC CCT GAG TAG TTA CTC CTG TG3'; SEQ ID NO: 4).

Results

Figure 6:
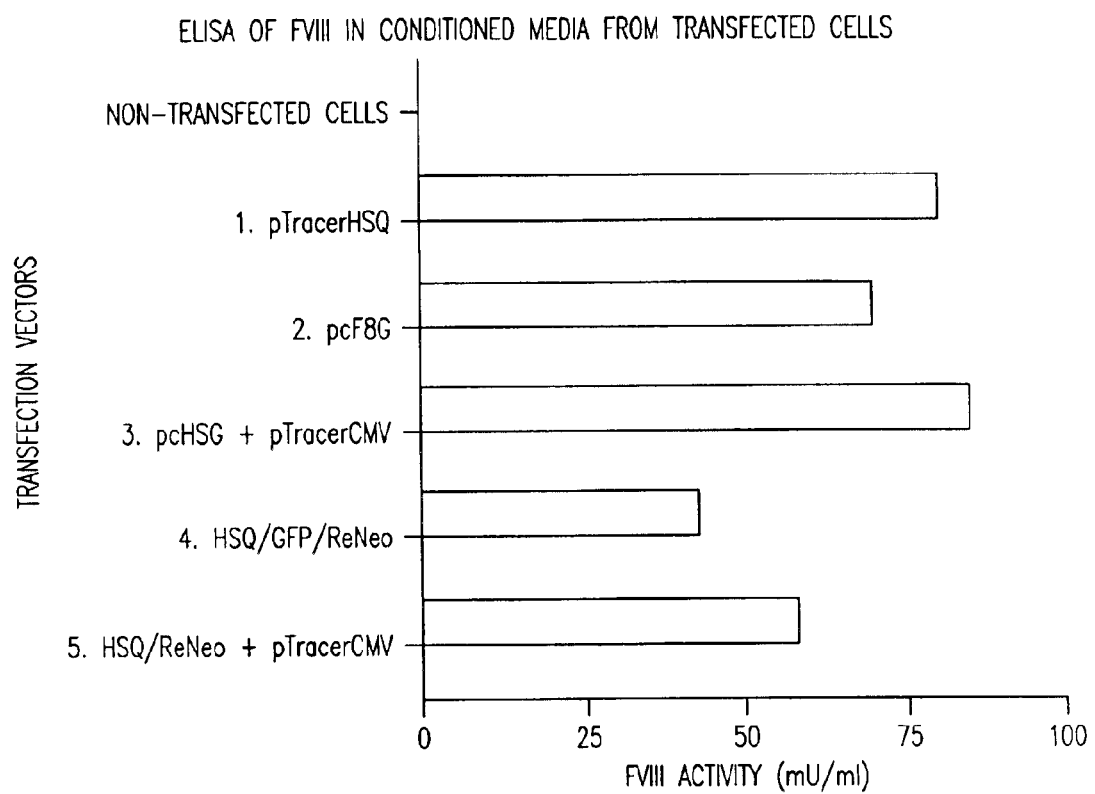
FIG. 6 shows factor VIII activity in conditioned media from cells transfected with various constructs (see Example 7).
Figure 7:
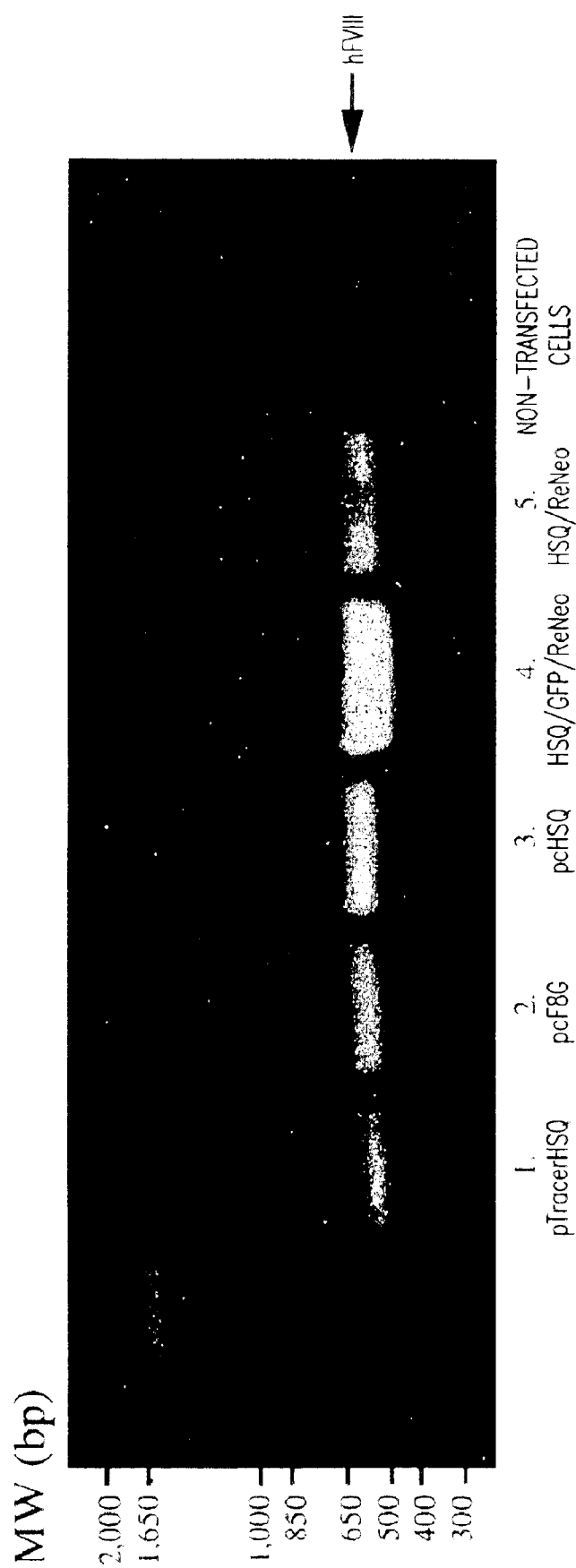
FIG. 7 depicts the results of a RT-PCR analysis for human FVIII mRNA in cells transfected with various constructs.

Three days after infection, hFVIII was detected in the supernatant of transfected cells (FIG. 6) but not in control cells. FIG. 7 shows the results of a RT-PCR analysis of RNA from those cells. The expression of hFVIII mRNA is increased in transfected cells relative to control cells.

At the end of 3 days, cells from 10 cm dishes were split into 2 10 cm dishes coated with 6 μg/ml of type I collagen and 50 μg/ml of fibronectin. The following day, cells were exposed to selection medium EGM-2 (Clonectis) containing 50 to 100 μg/ml of G418 or 50 μg/ml of Zeocin or both (Zeocin was used for selection of pTracerHSQ; G418 for pcFVIIIG and HSQ/GFP/ReNeo; and both Zeocin and G418 were used for cells subjected to cotransfection). Stable expression of hFVIII is detected in these cells after chemical selection.

All patents, patent applications and publications cited hereinabove, are incorporated by reference herein. While a preferred embodiment of the present invention has been described, it should be understood that various changes, adaptations and modifications may be made therein without departing from the spirit of the invention and the scope of the appended claims.

What is claimed is:

1. A process for expanding the population of endothelial cells obtained from peripheral blood comprising culturing, in contact with a collagen I-coated surface, mononuclear cells from a buffy coat layer obtained from peripheral mammalian blood, in the presence of a cell culture medium containing an effective amount of vascular endothelial growth factor (VEGF), and which medium is free of bovine brain extract, so as to expand the population of endothelial cells.

2. The process of claim 1 wherein the blood is human blood.

3. The process of claim 1 wherein said cell culture medium comprises heparin, dextran sulfate or mixtures thereof.

4. The process of claim 1 wherein the buffy coat mononuclear cells are obtained by washing cells from a buffy coat layer obtained from human blood in cell culture medium comprising 20% human male serum.

5. The process of claim 1 wherein the cell culture medium comprises human basic fibroblast growth factor.

6. The process of claim 1 or 5 wherein the cell culture medium comprises insulin-like growth factor.

7. The process of claim 1 or 5 wherein the cell culture medium contains human epidermal growth factor.

8. The process of claim 1 wherein the cell culture medium comprises about 0.5–10 vol-% fetal bovine serum.

9. The process of claim 1 further comprising trypsinizing the cultured cells at about $10^3$-fold expansion, collecting the trypsinized cells by centrifugation, resuspending the collected cells in cell culture medium, and subjecting the resuspended cells to culture in contact with a fibronectin- and gelatin-coated surface.

10. The process of claim 1 wherein the cultured cells are subjected to cryopreservation.

11. The process of claim 10 wherein the cells are frozen in a cryopreservation medium comprising fetal calf serum containing an effective amount of dimethylsulfoxide.

12. The process of claim 10 or 11 wherein the cryopreserved cells are thawed and culturing is resumed in said cell culture medium.

13. The process of claim 1 wherein the expanded population comprises microvascular endothelial cells.

14. The process of claim 13 wherein the microvascular endothelial cells are $CD34^+$, $CD36^+$ and express the P1H1 antigen.

15. The process of claim 1 wherein the cell culture medium comprises hydrocortisone.

16. The process of claim 1 wherein the cell culture medium comprises human serum.

17. The process of claim 1 which does not employ antibodies to obtain buffy coat mononuclear cells.

* * * * *

UNITED STATES PATENT AND TRADEMARK OFFICE
CERTIFICATE OF CORRECTION

PATENT NO. : 6,852,537 B2
DATED : February 8, 2005
INVENTOR(S) : Hebbel et al.

It is certified that error appears in the above-identified patent and that said Letters Patent is hereby corrected as shown below:

Title page,
Item [56], References Cited, OTHER PUBLICATIONS, "Gupta et al." reference, after "Research" delete ", vol. 230, pp. 244-251".
"Solovey et al." reference, after "anemia," delete "1997,"; and after "Medicine," delete "vol. 337,".
"Lin, Y., et al." reference, delete "Suppl" and insert -- Suppl. --, therefor.

Column 33,
Line 2, after "expanding" delete "the" and insert -- a --, therefor.

Signed and Sealed this

Twenty-second Day of November, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,852,537 B2 | Page 1 of 1 |
| APPLICATION NO. | : 09/865022 | |
| DATED | : February 8, 2005 | |
| INVENTOR(S) | : Robert P. Hebbel, Yi Lin and John S. Lollar | |

It is certified that error appears in the above-identified patent and that said Letters Patent is hereby corrected as shown below:

On the face page, in field (73), after "Regents of the University of Minnesota", insert -- , Minneapolis, MN (US) and --.

In column 1, line 12, after "HL 55174", delete "(now HL 30160)" and insert -- and HL 30160 --.

Signed and Sealed this

Twenty-ninth Day of August, 2006

JON W. DUDAS
*Director of the United States Patent and Trademark Office*

SEQUENCE LISTING

<160> NUMBER OF SEQ ID NOS: 4

<210> SEQ ID NO 1
<211> LENGTH: 5094
<212> TYPE: DNA
<213> ORGANISM: Artificial Sequence
<220> FEATURE:
<223> OTHER INFORMATION: The DNA sequence of HSQ/eGFP.

<400> SEQUENCE: 1

```
atgcaaatag agctctccac ctgcttcttt ctgtgccttt tgcgattctg ctttagtgcc       60
accagaagat actacctggg tgcagtggaa ctgtcatggg actatatgca aagtgatctc      120
ggtgagctgc ctgtggacgc aagatttcct cctagagtgc caaaatcttt tccattcaac      180
acctcagtcg tgtacaaaaa gactctgttt gtagaattca cggttcacct tttcaacatc      240
gctaagccaa ggccaccctg gatgggtctg ctaggtccta ccatccaggc tgaggtttat      300
gatacagtgg tcattacact taagaacatg gcttcccatc ctgtcagtct tcatgctgtt      360
ggtgtatcct actggaaagc ttctgaggga gctgaatatg atgatcagac cagtcaaagg      420
gagaaagaag atgataaagt cttccctggt ggaagccata catatgtctg gcaggtcctg      480
aaagagaatg gtccaatggc ctctgaccca ctgtgcctta cctactcata tctttctcat      540
gtggacctgg taaaagactt gaattcaggc ctcattggag ccctactagt atgtagagaa      600
gggagtctgg ccaaggaaaa gacacagacc ttgcacaaat ttatactact ttttgctgta      660
tttgatgaag ggaaaagttg gcactcagaa acaaagaact ccttgatgca ggatagggat      720
gctgcatctg ctcgggcctg gcctaaaatg cacacagtca atggttatgt aaacaggtct      780
ctgccaggtc tgattggatg ccacaggaaa tcagtctatt ggcatgtgat tggaatgggc      840
accactcctg aagtgcactc aatattcctc gaaggtcaca catttcttgt gaggaaccat      900
cgccaggcgt ccttggaaat ctcgccaata actttcctta ctgctcaaac actcttgatg      960
gaccttggac agtttctact gttttgtcat atctcttccc accaacatga tggcatggaa     1020
gcttatgtca agtagacag ctgtccagag gaaccccaac tacgaatgaa aaataatgaa     1080
gaagcggaag actatgatga tgatcttact gattctgaaa tggatgtggt caggtttgat     1140
gatgacaact ctccttcctt tatccaaatt cgctcagttg ccaagaagca tcctaaaact     1200
tgggtacatt acattgctgc tgaagaggag gactgggact atgctcccct agtcctcgcc     1260
cccgatgaca gaagttataa aagtcaatat ttgaacaatg ccctcagcg gattggtagg     1320
aagtacaaaa aagtccgatt tatggcatac acagatgaaa ccttaagac tcgtgaagct     1380
attcagcatg aatcaggaat cttgggacct ttactttatg gggaagttgg agacacactg     1440
ttgattatat ttaagaatca agcaagcaga ccatataaca tctaccctca cggaatcact     1500
gatgtccgtc ctttgtattc aaggagatta ccaaaaggtg taaacatttt gaaggatttt     1560
ccaattctgc caggagaaat attcaaatat aaatggacag tgactgtaga agatgggcca     1620
actaaatcag atcctcggtg cctgacccgc tattactcta gtttcgttaa tatggagaga     1680
gatctagctt caggactcat tggccctctc ctcatctgct acaaagaatc tgtagatcaa     1740
agaggaaacc agataatgtc agacaagagg aatgtcatcc tgttttctgt atttgatgag     1800
aaccgaagct ggtacctcac agagaatata caacgctttc tccccaatcc agctggagtg     1860
cagcttgagg atccagagtt ccaagcctcc aacatcatgc acagcatcaa tggctatgtt     1920
tttgatagtt tgcagttgtc agtttgtttg catgaggtgg catactggta cattctaagc     1980
```

-continued

```
attggagcac agactgactt cctttctgtc ttcttctctg gatatacctt caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga acctaggagc    2280
ttctctcaga atatggtgag caagggcgag gagctgttca ccggggtggt gcccatcctg    2340
gtcgagctgg acggcgacgt aaacggccac aagttcagcg tgtccggcga gggcgagggc    2400
gatgccacct acggcaagct gaccctgaag ttcatctgca ccaccggcaa gctgcccgtg    2460
ccctggccca ccctcgtgac caccctgacc tacggcgtgc agtgcttcag ccgctacccc    2520
gaccacatga agcagcacga cttcttcaag tccgccatgc ccgaaggcta cgtccaggag    2580
cgcaccatct tcttcaagga cgacggcaac tacaagaccc gcgccgaggt gaagttcgag    2640
ggcgacaccc tggtgaaccg catcgagctg aagggcatcg acttcaagga ggacggcaac    2700
atcctggggc acaagctgga gtacaactac aacagccaca acgtctatat catggccgac    2760
aagcagaaga acggcatcaa ggtgaacttc aagatccgcc acaacatcga ggacggcagc    2820
gtgcagctcg ccgaccacta ccagcagaac acccccatcg gcgacggccc cgtgctgctg    2880
cccgacaacc actacctgag cacccagtcc gccctgagca agaccccaa cgagaagcgc    2940 gatcacatgg tcctgctgga gttcgtgacc gccgccggga tcactctcgg catggacgag    3000
ctgtacaagt atccaccagt cttgaaacgc atcaacgggg aaataactcg tactactctt    3060
cagtcagatc aagaggaaat tgactatgat gataccatat cagttgaaat gaagaaggaa    3120
gattttgaca tttatgatga ggatgaaaat cagagccccc gcagctttca aaagaaaaca    3180
cgacactatt ttattgctgc agtggagagg ctctgggatt atgggatgag tagctcccca    3240
catgttctaa gaaacagggc tcagagtggc agtgtccctc agttcaagaa agttgttttc    3300
caggaattta ctgatggctc ctttactcag cccttatacc gtggagaact aaatgaacat    3360
ttgggactcc tggggccata taagagcaga gaagttgaag ataatatcat ggtaactttc    3420
agaaatcagg cctctcgtcc ctattccttc tattctagcc ttatttctta tgaggaagat    3480
cagaggcaag gagcagaacc tagaaaaaac tttgtcaagc ctaatgaaac caaaacttac    3540
ttttggaaag tgcaacatca tatggcaccc actaaagatg agtttgactg caaagcctgg    3600
gcttatttct ctgatgttga cctggaaaaa gatgtgcact caggcctgat ggacccctt    3660 ctggtctgcc acactaacac actgaaccct gctcatggga gacaagtgac agtacaggaa    3720
tttgctctgt ttttcaccat cttttgatgag accaaaagct ggtacttcac tgaaaatatg    3780
gaaagaaact gcagggctcc ctgcaatatc cagatggaag atcccacttt taaagagaat    3840
tatcgcttcc atgcaatcaa tggctacata atggatacac tacctggctt agtaatggct    3900
caggatcaaa ggattcgatg gtatctgctc agcatgggca gcaatgaaaa catccattct    3960
attcatttca gtggacatgt gttcactgta cgaaaaaaag aggagtataa aatggcactg    4020
tacaatctct atccaggtgt ttttgagaca gtggaaatgt taccatccaa agctggaatt    4080
tggcgggtgg aatgccttat tggcgagcat ctacatgctg ggatgagcac acttttctg    4140 gtgtacagca ataagtgtca gactcccctg ggaatggctt ctggacacat tagagatttt    4200
cagattacag cttcaggaca atatggacag tgggcccaa agctggccag acttcattat    4260
tccggatcaa tcaatgcctg gagcaccaag gagcccttt cttggatcaa ggtggatctg    4320
```

-continued

```
ttggcaccaa tgattattca cggcatcaag acccagggtg cccgtcagaa gttctccagc    4380
ctctacatct ctcagtttat catcatgtat agtcttgatg ggaagaagtg gcagacttat    4440
cgaggaaatt ccactggaac cttaatggtc ttctttggca atgtggattc atctgggata    4500
aaacacaata ttttttaaccc tccaattatt gctcgataca tccgtttgca cccaactcat    4560
tatagcattc gcagcactct tcgcatggag ttgatgggct gtgatttaaa tagttgcagc    4620
atgccattgg gaatggagag taaagcaata tcagatgcac agattactgc ttcatcctac    4680
tttaccaata tgtttgccac ctggtctcct tcaaaagctc gacttcacct ccaagggagg    4740
agtaatgcct ggagacctca ggtgaataat ccaaaagagt ggctgcaagt ggacttccag    4800
aagacaatga agtcacagg agtaactact cagggagtaa aatctctgct taccagcatg    4860
tatgtgaagg agttcctcat ctccagcagt caagatggcc atcagtggac tctctttttt    4920
cagaatggca agtaaaggt ttttcaggga atcaagact ccttcacacc tgtggtgaac    4980
tctctagacc caccgttact gactcgctac cttcgaattc accccagag ttgggtgcac    5040 cagattgccc tgaggatgga ggttctgggc tgcgaggcac aggacctcta ctga    5094
```

<210> SEQ ID NO 2
<211> LENGTH: 12445
<212> TYPE: DNA
<213> ORGANISM: Artificial Sequence
<220> FEATURE:
<223> OTHER INFORMATION: The DNA sequence of HSQRENeo.

<400> SEQUENCE: 2

```
gaattccgga attccagctt gctgtggaat gtgtgtcagt tagggtgtgg aaagtcccca      60
ggctccccag caggcagaag tatgcaaagc atgcatctca attagtcagc aaccaggtgt     120
ggaaagtccc caggctcccc agcaggcaga agtatgcaaa gcatgcatct caattagtca     180
gcaaccatag tcccgcccct aactccgccc atcccgcccc taactccgcc cagttccgcc     240
cattctccgc cccatggctg actaattttt tttatttatg cagaggccga ggccgcctcg     300
gcctctgagc tattccagaa gtagtgagga ggcttttttg gagggtcct cctcgtatag     360 aaactcggac cactctgaga cgaaggctcg cgtccaggcc agcacgaagg aggctaagtg     420 ggagggtag cggtcgttgt ccactagggg gtccactcgc tccagggtgt gaagacacat     480
gtcgccctct tcggcatcaa ggaaggtgat tggtttatag gtgtaggcca cgtgaccggg     540
tgttcctgaa gggggggtat aaagggggt ggggcgcgt tcgtcctcac tctcttccgc     600
atcgctgtct gcgagggcca gctgttgggc tcgcggttga ggacaaactc ttcgcggtct     660
ttccagtact cttggatcgg aaacccgtcg gcctccgaac ggtactccgc caccgaggga     720
cctgagcgag tccgcatcga ccggatcgga aacctctcg agccaccatg caaatagagc     780
tctccacctg cttctttctg tgccttttgc gattctgctt tagtgccacc agaagatact     840
acctgggtgc agtggaactg tcatgggact atatgcaaag tgatctcggt gagctgcctg     900
tggacgcaag atttcctcct agagtgccaa atcttttcc attcaacacc tcagtcgtgt     960
acaaaaagac tctgtttgta gaattcacgg ttcaccttt caacatcgct aagccaaggc    1020
caccctggat gggtctgcta ggtcctacca tccaggctga ggtttatgat acagtggtca    1080
ttacacttaa gaacatggct tcccatcctg tcagtcttca tgctgttggt gtatcctact    1140
ggaaagcttc tgagggagct gaatatgatg atcagaccag tcaaagggag aagaagatg    1200 ataaagtctt ccctggtgga agccatacat atgtctggca ggtcctgaaa gagaatggtc    1260
caatggcctc tgacccactg tgccttacct actcatatct ttctcatgtg gacctggtaa    1320
```

-continued

```
aagacttgaa ttcaggcctc attggagccc tactagtatg tagagaaggg agtctggcca    1380
aggaaaagac acagaccttg cacaaattta tactactttt tgctgtattt gatgaaggga    1440
aaagttggca ctcagaaaca aagaactcct tgatgcagga tagggatgct gcatctgctc    1500
gggcctggcc taaaatgcac acagtcaatg gttatgtaaa caggtctctg ccaggtctga    1560
ttggatgcca caggaaatca gtctattggc atgtgattgg aatgggcacc actcctgaag    1620
tgcactcaat attcctcgaa ggtcacacat tcttgtgag gaaccatcgc caggcgtcct    1680
tggaaatctc gccaataact ttccttactg ctcaaacact cttgatggac cttggacagt    1740
ttctactgtt ttgtcatatc tcttcccacc aacatgatgg catggaagct tatgtcaaag    1800
tagacagctg tccagaggaa ccccaactac gaatgaaaaa taatgaagaa gcggaagact    1860
atgatgatga tcttactgat tctgaaatgg atgtggtcag gtttgatgat gacaactctc    1920
cttcctttat ccaaattcgc tcagttgcca agaagcatcc taaaacttgg gtacattaca    1980
ttgctgctga agaggaggac tgggactatg ctcccttagt cctcgccccc gatgacagaa    2040
gttataaaag tcaatatttg aacaatggcc ctcagcggat tggtaggaag tacaaaaaag    2100
tccgatttat ggcatacaca gatgaaacct ttaagactcg tgaagctatt cagcatgaat    2160
caggaatctt gggacccttta ctttatgggg aagttggaga cacactgttg attatattta    2220
agaatcaagc aagcagacca tataacatct accctcacgg aatcactgat gtccgtcctt    2280
tgtattcaag gagattacca aaggtgtaa acatttgaa ggattttcca attctgccag    2340
gagaaatatt caaatataaa tggacagtga ctgtagaaga tgggccaact aaatcagatc    2400
ctcggtgcct gacccgctat tactctagtt tcgttaatat ggagagagat ctagcttcag    2460
gactcattgg ccctctcctc atctgctaca agaatctgt agatcaaaga ggaaaccaga    2520
taatgtcaga caagaggaat gtcatcctgt tttctgtatt tgatgagaac cgaagctggt    2580
acctcacaga gaatatacaa cgcttttctcc ccaatccagc tggagtgcag cttgaggatc    2640
cagagttcca agcctccaac atcatgcaca gcatcaatgg ctatgttttt gatagtttgc    2700
agttgtcagt ttgtttgcat gaggtggcat actggtacat tctaagcatt ggagcacaga    2760
ctgacttcct ttctgtcttc ttctctggat ataccttcaa acacaaaatg gtctatgaag    2820
acacactcac cctattccca ttctcaggag aaactgtctt catgtcgatg gaaaacccag    2880
gtctatggat tctggggtgc acaactcag actttcggaa cagaggcatg accgccttac    2940
tgaaggtttc tagttgtgac aagaacactg gtgattatta cgaggacagt tatgaagata    3000
tttcagcata cttgctgagt aaaaacaatg ccattgaacc taggagcttc tctcagaatc    3060
caccagtctt gaaacgccat caacgggaaa taactcgtac tactcttcag tcagatcaag    3120
aggaaattga ctatgatgat accatatcag ttgaaatgaa gaaggaagat tttgacattt    3180
atgatgagga tgaaaatcag agccccgca gctttcaaaa gaaaacacga cactattta    3240 ttgctgcagt ggagaggctc tgggattatg ggatgagtag ctccccacat gttctaagaa    3300
acagggctca gagtggcagt gtccctcagt tcaagaaagt tgttttccag gaatttactg    3360
atggctcctt tactcagccc ttataccgtg agaactaaa tgaacatttg ggactcctgg    3420
ggccatatat aagagcagaa gttgaagata atatcatggt aactttcaga aatcaggcct    3480
ctcgtcccta ttccttctat tctagcctta tttcttatga ggaagatcag aggcaaggag    3540
cagaacctag aaaaaacttt gtcaagccta atgaaaccaa aacttacttt tggaaagtgc    3600
aacatcatat ggcacccact aaagatgagt ttgactgcaa agcctgggct tatttctctg    3660
```

-continued

```
atgttgacct ggaaaaagat gtgcactcag gcctgattgg accccttctg gtctgccaca    3720
ctaacacact gaaccctgct catgggagac aagtgacagt acaggaattt gctctgtttt    3780
tcaccatctt tgatgagacc aaaagctggt acttcactga aaatatggaa agaaactgca    3840
gggctccctg caatatccag atggaagatc ccacttttaa agagaattat cgcttccatg    3900
caatcaatgg ctacataatg gatacactac ctggcttagt aatggctcag gatcaaagga    3960
ttcgatggta tctgctcagc atgggcagca atgaaaacat ccattctatt catttcagtg    4020
gacatgtgtt cactgtacga aaaaagagg agtataaaat ggcactgtac aatctctatc    4080
caggtgtttt tgagacagtg gaaatgttac catccaaagc tggaatttgg cgggtggaat    4140
gccttattgg cgagcatcta catgctggga tgagcacact ttttctggtg tacagcaata    4200
agtgtcagac tcccctggga atggcttctg gacacattag agattttcag attacagctt    4260
caggacaata tggacagtgg gccccaaagc tggccagact tcattattcc ggatcaatca    4320
atgcctggag caccaaggag ccttttctt ggatcaaggt ggatctgttg caccaatga    4380
ttattcacgg catcaagacc cagggtgccc gtcagaagtt ctccagcctc tacatctctc    4440
agtttatcat catgtatagt cttgatggga agaagtggca gacttatcga ggaaattcca    4500
ctggaacctt aatggtcttc tttggcaatg tggattcatc tgggataaaa cacaatattt    4560
ttaaccctcc aattattgct cgatacatcc gtttgcaccc aactcattat agcattcgca    4620
gcactcttcg catggagttg atgggctgtg atttaaatag ttgcagcatg ccattgggaa    4680
tggagagtaa agcaatatca gatgcacaga ttactgcttc atcctacttt accaatatgt    4740
ttgccacctg gtctccttca aaagctcgac ttcacctcca agggaggagt aatgcctgga    4800
gacctcaggt gaataatcca aaagagtggc tgcaagtgga cttccagaag acaatgaaag    4860
tcacaggagt aactactcag ggagtaaaat ctctgcttac cagcatgtat gtgaaggagt    4920
tcctcatctc cagcagtcaa gatggccatc agtggactct cttttttcag aatggcaaag    4980
taaaggtttt tcagggaaat caagactcct tcacacctgt ggtgaactct ctagacccac    5040
cgttactgac tcgctacctt cgaattcacc cccagagttg ggtgcaccag attgccctga    5100
ggatggaggt tctgggctgc gaggcacagg acctctactg agggcggccg ctgcagcacc    5160
tgccactgcc gtcacctctc cctcctcagc tccagggcag tgtccctccc tggcttgcct    5220
tctacctttg tgctaaatcc tagcagacac tgccttgaag cctcctgaat taactatcat    5280
cagtcctgca tttctttggt gggggccag gagggtgcat ccaatttaac ttaactctta    5340
cctattttct gcagctgctc ccagattact ccttccttcc aatataacta ggcaaaaaga    5400
agtgaggaga aacctgcatg aaagcattct tccctgaaaa gttaggcctc tcagagtcac    5460
cacttcctct gttgtagaaa aactatgtga tgaaactttg aaaagatat ttatgatgtt    5520
aacatttcag gttaagcctc atacgtttaa aataaaactc tcagttgttt attatcctga    5580
tcaagcatgg aacaaagcat gtttcaggat cagatcaata caatcttgga gtcaaaaggc    5640
aaatcatttg gacaatctgc aaaatggaga gaatacaata actactacag taaagtctgt    5700
ttctgcttcc ttacacatag atataattat gttatttagt cattatgagg ggcacattct    5760
tatctccaaa actagcattc ttaaactgag aattatagat ggggttcaag aatccctaag    5820
tccccctgaaa ttatataagg cattctgtat aaatgcaaat gtgcattttt ctgacgagtg    5880
tccatagata tgggacatat gacgtgagct cagatctttg tgaaggaacc ttacttctgt    5940
ggtgtgacat aattggacaa actacctaca gagatttaaa gctctaaggt aaatataaaa    6000
tttttaagtg tataatgtgt taaactactg attctaattg tttgtgtatt ttagattcca    6060
```

```
acctatggaa ctgatgaatg ggagcagtgg tggaatgcct ttaatgagga aaacctgttt      6120
tgctcagaag aaatgccatc tagtgatgat gaggctactg ctgagtgtga acattctact      6180
cctccaaaaa agaagagaaa ggtagaagac cccaaggact ttccttcaga attgctaagt      6240 ttttgagtc atgctgtgtt tagtaataga actcttgctt gctttgctat ttacaccaca       6300
aaggaaaaag ctgcactgct atacaagaaa attatggaaa atattctgt aacctttata       6360 agtaggcata acagttataa tcataacata ctgttttttc ttactccaca caggcataga     6420
gtgtctgcta ttaataacta tgctcaaaaa ttgtgtacct ttagcttttt aatttgtaaa      6480
ggggttaata aggaatattt gatgtatagt gccttgacta gagatcataa tcagccatac      6540
cacatttgta gaggttttac ttgctttaaa aaacctccca cacctccccc tgaacctgaa     6600
acataaaatg aatgcaattg ttgttgttaa cttgtttatt gcagcttata atggttacaa    6660
ataaagcaat agcatcacaa atttcacaaa taaagcattt ttttcactgc attctagttg    6720
tggtttgtcc aaactcatca atgtatctta tcatgtctgg atcctctacg ccggacgcat   6780
cgtggccggc atcaccggcg ccacaggtgc ggttgctggc gcctatatcg ccgacatcac    6840
cgatggggaa gatcgggctc gccacttcgg gctcatgagc gcttgtttcg gcgtgggtat   6900
ggtggcaggc ccgtggccgg gggactgttg ggcgccatct ccttgcatgc accattcctt    6960
gcggcggcgg tgctcaacgg cctcaaccta ctactgggct gcttcctaat gcaggagtcg    7020
cataagggag agcgtcgaaa ttctcatgtt tgacagctta tcatcggcgc agcaccatgg   7080
cctgaaataa cctctgaaag aggaacttgg ttaggtacct tctgaggcgg aaagaaccag    7140
ctgtggaatg tgtgtcagtt agggtgtgga agtccccag gctggggagc aggcagaagt     7200
atgcaaagca tgcatctcaa ttagtcagca accaggtgtg gaaagtcccc aggctcccca   7260
gcaggcagaa gtatgcaaag catgcatctc aattagtcag caaccatagt cccgccccta    7320
actccgccca tcccgcccct aactccgccc agttccgccc attctccgcc ccatggctga    7380 ctaattttt ttatttatgc agaggccgag gccgcctcgg cctctgagct attccagccg    7440
tagtgaggag gcttttttgg aggcctaggc ttttgcaaaa agcttcacgc tgccgcaagc    7500
actcagggcg caagggctgc taaaggaagc ggaacacgta gaaagccagt ccgcagaaac   7560
ggtgctgacc ccggatgaat gtcagctact gggctatctg gacaagggaa aacgcaagcg    7620
caaagagaaa gcaggtagct tgcagtgggc ttacatggcg atagctagac tgggcggttt    7680
tatgacagca agcgaaccg gaattgccag ctggggcgcc ctctggtaag gttgggaagc     7740
cctgcaaagt aaactggatg ctttcttgc cgccaaggat ctgatggcgc aggggatcaa    7800
gatctgatca agagacagga tgaggatcgt ttcgcatgat tgaacaagat ggattgcacg   7860
caggttctcc ggccgcttgg gtggagaggc tattcggcta tgactgggca acagacaa     7920 tcggctgctc tgatgccgcc gtgttccggc tgtcagcgca ggggcgcccg gttctttttg    7980
tcaagaccga cctgtccggt gccctgaatg aactgcagga cgaggcagcg cggctatcgt    8040
ggctggccac gacgggcgtt ccttgcgcag ctgtgctcga cgttgtcact gaagcgggaa    8100
gggactggct gctattgggc gaagtgccgg ggcaggatct cctgtcatct caccttgctc    8160
ctgccgagaa agtatccatc atggctgatg caatgcggcg gctgcatacg cttgatccgg    8220
ctacctgccc attcgaccac caagcgaaac atcgcatcga gcgagcacgt actcggatgg    8280
aagccggtct tgtcgatcag gatgatctgg acgaagagca tcaggggctc gcgccagccg    8340
aactgttcgc caggctcaag gcgcgcatgc ccgacggcga ggatctcgtc gtgacccatg    8400
```

```
gcgatgcctg cttgccgaat atcatggtgg aaaatggccg cttttctgga ttcatcgact   8460
gtggccggct gggtgtggcg gaccgctatc aggacatagc gttggctacc cgtgatattg   8520
ctgaagagct tggcggcgaa tgggctgacc gcttcctcgt gctttacggt atcgccgctc   8580
ccgattcgca gcgcatcgcc ttctatcgcc ttcttgacga gttcttctga gcgggactct   8640
ggggttcgaa atgaccgacc aagcgacgcc caacctgcca tcacgagatt tcgattccac   8700
cgccgccttc tatgaaaggt tgggcttcgg aatcgttttc cgggacgccg gctggatgat   8760
cctccagcgc gggatctca tgctggagtt cttcgcccac cccgggctcg atccctcgc    8820
gagttggttc agctgctgcc tgaggctgga cgacctcgcg gagttctacc ggcagtgcaa   8880
atccgtcggc atccaggaaa ccagcagcgg ctatccgcgc atccatgccc cgaactgca    8940
ggagtgggga ggcacgatgg ccgctttggt cccggatctt tgtgaaggaa ccttacttct   9000
gtggtgtgac ataattggag aaactaccta cagagattta agctctaag gtaaatataa    9060
aatttttaag tgtataatgt gttaaactac tgattctaat tgtttgtgta ttttagattc   9120
caacctatgg aactgatgaa tgggagcagt ggtggaatgc ctttaatgag gaaaacctgt   9180
tttgctcaga gaaatgcca tctagtgatg atgaggctac tgctgactct caacattcta   9240
ctcctccaaa aagaagaga aggtagaag accccaagga cttccttca gaattgctaa      9300
gttttttgag tcatgctgtg tttagtaata gaactcttgc ttgctttgct atttacacca   9360
caaaggaaaa agctgcactg ctatacaaga aaattatgga aaaatattct gtaaccttta   9420
taagtaggca taacagttat aatcataaca tactgttttt tcttactcca cacaggcata   9480
gagtgtctgc tattaataac tatgctcaaa aattgtgtac ctttagcttt ttaatttgta   9540
aagggggttaa taaggaatat ttgatgtata gtgccttgac tagagatcat aatcagccat   9600
accacatttg tagaggtttt acttgcttta aaaaacctcc cacacctccc cctgaacctg   9660
aaacataaaa tgaatgcaat tgttgttgtt aacttgttta ttgcagctta taatggttac   9720
aaataaagca atagcatcac aaatttcaca aataaagcat ttttttcact gcattctagt   9780
tgtggtttgt ccaaactcat caatggtatc ttatcatgtc tggatctcga ccgagcccct   9840
gagagccttc aacccagtca gctccttccg gtgggcgcgg ggcatgacta tcgtcgccgc   9900
acttatgact gtcttcttta tcatgcaact cgtaggacag gtgccggcag cgctctgggt   9960
catttcgggc gaggaccgct ttcgctggag cgcgacgatg atcggcctgt cgcttgcggt  10020
attcggaatc ttgcacgccc tcgctcaagc cttcgtcact ggtcccgcca ccaaacgttt  10080
cggcgagaag caggccatta tcgccggcat ggcggccgac gcgctgggct acgtcttgct  10140
ggcgttcgcg acgcgaggct ggatggcctt ccccattatg attcttctcg cttccggcgg  10200
catcgggatg cccgcgttgc aggccatgct gtccaggcag gtagatgacg accatcaggg  10260
acagcttcaa ggatcgctcg cggctcttac cagcctaact tcgatcactg gaccgctgat  10320
cgtcacggcg atttatgccg cctcggcgag cacatggaac gggttggcat ggattgtagg  10380
cgccgccta ccttgtct gcctccccgc gttgcgtcgc ggtgcatgga gccgggccac    10440
ctcgacctga atggaagccg gcggcacctc gctaacggat tcaccactcc aagaattgga  10500
gccaatcaat tcttgcggag aactgtgaat gcgcaaacca acccttggca gaacatatcc  10560
atcgcgtccg ccatctccag cagccgcacg cggcgcatct cgggcgcgt tgctggcgtt  10620
tttccatagg ctccgccccc ctgacgagca tcacaaaaat cgacgctcaa gtcagaggtg  10680
gcgaaacccg acaggactat aaagatacca ggcgtttccc cctggaagct ccctcgtgcg  10740
ctctcctgtt ccgaccctgc cgcttaccgg atacctgtcc gcctttctcc cttcgggaag  10800
```

```
cgtggcgctt tctcaatgct cacgctgtac ctatctcagt tcggtgtacc tcgttcgctc    10860
caagctgggc tgtgtgcacg aaccccccgt tcagcccgac cgctgcgcct tatccggtaa    10920
ctatcgtctt gagtccaacc cggtaagaca cgacttatcg ccactggcag cagccactgg    10980
taacaggatt agcagagcga ggtatgtagg cggtgctaca gagttcttga agtggtggcc    11040
taactacggc tacactagaa ggacagtatt tggtatctgc gctctgctga agccagttac    11100
cttcggaaaa agagttggta gctcttgatc cggcaaacaa accaccgctg gtagcggtgg    11160 ttttttttgtt tgcaagcagc agattacgcg cagaaaaaaa ggatctcaag aagatccttt    11220
gatcttttct acgggtctg acgctcagtg aacgaaaac tcacgttaag ggattttggt    11280
catgagatta tcaaaaagga tcttcaccta gatccttta aattaaaaat gaagttttaa    11340
atcaatctaa agtatatatg agtaaacttg gtctgacagt taccaatgct taatcagtga    11400
ggcacctatc tcagcgatct gtctatttcg ttcatccata gttgcctgac tccccgtcgt    11460
gtagataact acgatacggg agggcttacc atctggcccc agtgctgcaa tgataccgcg    11520
agacccacgc tcaccggctc cagatttatc agcaataaac cagccagcca gaagggccga    11580
gcgcagaagt ggtcctgcaa ctttatccgc ctccatccag tctattaatt gttgccggga    11640
agctagagta gtagttcgc cagttaatag tttgcgcaac gttgttgcca ttgctgcagg    11700
catcgtggtg tcacgctcgt cgtttggtat ggcttcattc agctccggtt cccaacgatc    11760
aaggcgagtt acatgatccc ccatgttgtg caaaaaagcg gttagctcct tcggtcctcc    11820
gatcgttgtc agaagtaagt tggccgcagt gttatcactc atggttatgg cagcactgca    11880
taattctctt actgtcatgc catccgtaag atgcttttct gtgactggtg agtactcaac    11940
caagtcattc tgagaatagt gtatgcggcg accgagttgc tcttgcccgg cgtcaacacg    12000
ggataatacc gcgccacata gcagaacttt aaaagtgctc atcattggaa aacgttcttc    12060
ggggcgaaaa ctctcaagga tcttaccgct gttgagatcc agttcgatgt aacccactcg    12120
tgcacccaac tgatcttcag catctttac tttcaccagc gtttctgggt gagcaaaaac    12180
aggaaggcaa aatgccgcaa aaagggaat aagggcgaca cggaaatgtt gaatactcat    12240
actcttcctt tttcaatatt attgaagcat ttatcagggt tattgtctca tgagcggata    12300
catatttgaa tgtatttaga aaataaaca aataggggtt ccgcgcacat ttccccgaaa    12360
agtgccacct gacgtctaag aaaccattat tatcatgaca ttaacctata aaaataggcg    12420
tatcacgagg ccctttcgtc ttcaa    12445
```

<210> SEQ ID NO 3
<211> LENGTH: 23
<212> TYPE: DNA
<213> ORGANISM: Homo sapiens

<400> SEQUENCE: 3
gcccttttct tggatcaagg tgg    23

<210> SEQ ID NO 4
<211> LENGTH: 23
<212> TYPE: DNA
<213> ORGANISM: Homo sapiens

<400> SEQUENCE: 4
ctccctgagt agttactcct gtg    23